United States Patent
DeLuca et al.

[11] Patent Number: 6,127,559
[45] Date of Patent: *Oct. 3, 2000

[54] 2-ALKYL-19-NOR-VITAMIN D COMPOUNDS

[75] Inventors: Hector F. DeLuca, Deerfield, Wis.; Rafal R. Sicinski, Warsaw, Poland

[73] Assignee: Wisconsin Alumni Research Foundation, Madison, Wis.

[*] Notice: This patent is subject to a terminal disclaimer.

[21] Appl. No.: 09/135,463

[22] Filed: Aug. 17, 1998

Related U.S. Application Data

[63] Continuation-in-part of application No. 08/819,694, Mar. 17, 1997, Pat. No. 5,945,410.

[51] Int. Cl.$^7$ .......................... C07C 401/00; A61K 31/59
[52] U.S. Cl. .......................... 552/653; 552/653; 514/167
[58] Field of Search .......................... 552/653; 514/167

[56] References Cited

U.S. PATENT DOCUMENTS

| | | | |
|---|---|---|---|
| 4,666,634 | 5/1987 | Miyamoto et al. | 260/397 |
| 5,086,191 | 2/1992 | DeLuca et al. | 552/653 |

(List continued on next page.)

FOREIGN PATENT DOCUMENTS

| | | | |
|---|---|---|---|
| 0184206 | 12/1985 | European Pat. Off. | C07C 172/00 |
| 0387077 | 9/1990 | European Pat. Off. | C07C 401/00 |
| 0516410 | 12/1992 | European Pat. Off. | C07C 401/00 |

OTHER PUBLICATIONS

Posner et al, "Stereocontrolled Synthesis of a Trihydroxylated A ring as an Immediate Precursor to $1\alpha,2\alpha,25$–Trihydroxyvitamin $D_3$." J. Org. Chem. 56, pp. 4339–4341, Apr. 15, 1991.

(List continued on next page.)

*Primary Examiner*—Jose' G. Dees
*Assistant Examiner*—Sabiha N. Qazi

*Attorney, Agent, or Firm*—Andrus, Sceales, Starke & Sawall

[57] ABSTRACT

This invention provides a novel class of vitamin D related compounds, namely, the 2-alkyl-19-nor-vitamin D derivatives, as well as a general method for their chemical synthesis. The compounds have the formula:

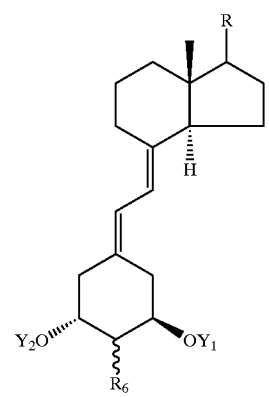

where $Y_1$ and $Y_2$, which may be the same or different, are each selected from the group consisting of hydrogen and a hydroxy-protecting group, $R_6$ is selected from the group consisting of alkyl, hydroxyalkyl and fluoroalkyl, and where the group R represents any of the typical side chains known for vitamin D type compounds. These 2-substituted compounds, especially the $2\alpha$-methyl and the $2\alpha$-methyl-20S derivatives, are characterized by relatively low intestinal calcium transport activity and high bone calcium mobilization activity resulting in novel therapeutic agents for the treatment of diseases where bone formation is desired, particularly low bone turnover osteoporosis. These compounds also exhibit pronounced activity in arresting the proliferation of undifferentiated cells and inducing their differentiation to the monocyte thus evidencing use as anti-cancer agents and for the treatment of diseases such as psoriasis.

43 Claims, 6 Drawing Sheets

U.S. PATENT DOCUMENTS

| | | | |
|---|---|---|---|
| 5,237,110 | 8/1993 | DeLuca et al. | 568/665 |
| 5,246,925 | 9/1993 | DeLuca et al. | 514/167 |
| 5,536,713 | 7/1996 | DeLuca et al. | 514/167 |
| 5,587,497 | 12/1996 | DeLuca et al. | 552/653 |
| 5,843,928 | 12/1998 | DeLuca et al. | 514/167 |
| 5,936,133 | 8/1999 | DeLuca et al. | 568/828 |

OTHER PUBLICATIONS

"Chemistry of Synthetic High Polymers," Chemical Abstracts, vol. 110, No. 10, Mar. 6, 1989.

Okano et al, "Regulatory Activities of 2β–(3–Hydroxypropoxy)–1α,25–Dihydroxyvitamin $D_3$. A Novel Synthetic Vitamin $D_3$ Derivative, on Calcium Matabolism," Biochemical and Biophysical Research Communications, vol. 163, No. 3, pp. 1444–1449, Sep. 29, 1989.

Bouillon et al, "Biologic Activity of Dihydroxylated 19–Nor–(Pre) Vitamin $D_3$," Bioactivity of 19–Nor–Pre D, vol. 8, No. 8, pp. 1009–1015, 1993.

Sarandeses et al, "Synthesis of 1α,25–Dihydroxy–19–Norprevitamin $D_3$," Tetrahedron Letters, pp. 5445–5448, Apr. 1992.

Perlman et al, "1α,25–Dihydroxy–19–Nor–Vitamin $D_3$. A Novel Vitamin D–Related Compound with Potential Therapeutic Activity," Tetrahedron Letters, vol. 31, No. 13, pp. 1823–1824, Feb. 1990.

Baggionlini et al, "Stereocontrolled Total Synthesis of 1α,25–Dihydroxy–cholecalciferol and 1α,25–Dihydroxy-erocalciferol," J. Org. Chem., 51, pp. 3098–3108, 1996.

Kiegiel et al, "Chemical Conversion of Vitamin $D_3$ to its 1,5–Dihydroxy Metabolite," Tetrahedron Letters, vol. 31, No. 43, pp. 6057–6060, 1991.

2-ALKYL-19-NOR-VITAMIN D COMPOUNDS

CROSS-REFERENCE TO RELATED APPLICATIONS

This application is a continuation-in-part of application Ser. No. 08/819,694 filed Mar. 17, 1997, now U.S. Pat. No. 5,945,410.

STATEMENT REGARDING FEDERALLY SPONSERED RESEARCH OR DEVELOPMENT

This invention was made with United States government support awarded by the following agencies:

NIH DK 14881-26S1

The United States has certain rights in this invention.

BACKGROUND OF THE INVENTION

This patent invention relates to vitamin D compounds, and more particularly to vitamin D derivatives substituted at the carbon 2 position.

The natural hormone, $1\alpha,25$-dihydroxyvitamin $D_3$ and its analog in ergosterol series, i.e. $1\alpha,25$-dihydroxyvitamin $D_2$ are known to be highly potent regulators of calcium homeostasis in animals and humans, and more recently their activity in cellular differentiation has been established, Ostrem et al., Proc. Natl. Acad. Sci. USA, 84, 2610 (1987). Many structural analogs of these metabolites have been prepared and tested, including $1\alpha$-hydroxyvitamin $D_3$, $1\alpha$-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies.

Recently, a new class of vitamin D analogs has been discovered, i.e. the so called 19-nor-vitamin D compounds, which are characterized by the replacement of the A-ring exocyclic methylene group (carbon 19), typical of the vitamin D system, by two hydrogen atoms. Biological testing of such 19-nor-analogs (e.g., $1\alpha,25$-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of $1\alpha,25$-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of $1\alpha,25$-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

Recently, 2-substituted analogs of $1\alpha,25$-dihydroxy-19-norvitamin $D_3$ have also been synthesized, i.e. compounds substituted at 2-position with hydroxy or alkoxy groups (DeLuca et al., U.S. Pat. No. 5,536,713), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, their analogs which are characterized by the presence of an alkyl (particularly methyl) substituent at the carbon 2 (C-2), i.e. 2-alkyl-19-nor-vitamin D compounds, and particularly 2-methyl-19-nor-vitamin D compounds, have now been synthesized and tested. Such vitamin D analogs seemed interesting targets because the relatively small alkyl (particularly methyl) group at C-2 should not interfere with binding to the vitamin D receptor. On the other hand it is obvious that a change of conformation of the cyclohexanediol ring A can be expected for these new analogs.

BRIEF SUMMARY OF THE INVENTION

A class of $1\alpha$-hydroxylated vitamin D compounds not known heretofore are the 19-nor-vitamin D analogs having an alkyl (particularly methyl) group at the 2-position, i.e. 2-alkyl-19-nor-vitamin D compounds, particularly 2-methyl-19-nor-vitamin D compounds.

Structurally these novel analogs are characterized by the general formula I shown below:

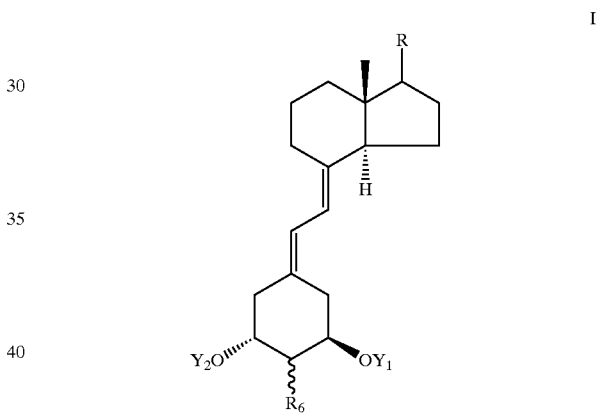

where $Y_1$ and $Y_2$, which may be the same or different, are each selected from the group consisting of hydrogen and a hydroxy-protecting group, $R_6$ is selected from the group consisting of alkyl, hydroxyalkyl and fluoroalkyl, and where the group R represents any of the typical side chains known for vitamin D type compounds.

More specifically R can represent a saturated or unsaturated hydrocarbon radical of 1 to 35 carbons, that may be straight-chain, branched or cyclic and that may contain one or more additional substituents, such as hydroxy- or protected-hydroxy groups, fluoro, carbonyl, ester, epoxy, amino or other heteroatomic groups. Preferred side chains of this type are represented by the structure below

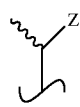

where the stereochemical center (corresponding to C-20 in steroid numbering) may have the R or S configuration, (i.e. either the natural configuration about carbon 20 or the 20-epi configuration), and where Z is selected from Y, —OY, —CH$_2$OY, —C≡CY and —CH=CHY, where the double bond may have the cis or trans geometry, and where Y is selected from hydrogen, methyl, —COR$^5$ and a radical of the structure:

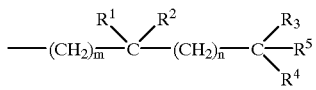

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group, =CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —CH(R$^3$)—, or —CH(R$^2$)— at positions 20, 22, and 23, respectively, may be replaced by an oxygen or sulfur atom.

The wavy lines to the substituents at C-2 and at C-20 indicate that the carbon 2 and carbon 20 may have either the R or S configuration.

Specific important examples of side chains with natural 20R-configuration are the structures represented by formulas (a), b), (c), (d) and (e) below. i.e. the side chain as it occurs in 25-hydroxyvitamin D$_3$ (a); vitamin D$_3$ (b); 25-hydroxyvitamin D$_2$ (c); vitamin D$_2$ (d); and the C-24 epimer of 25-hydroxyvitamin D$_2$ (e):

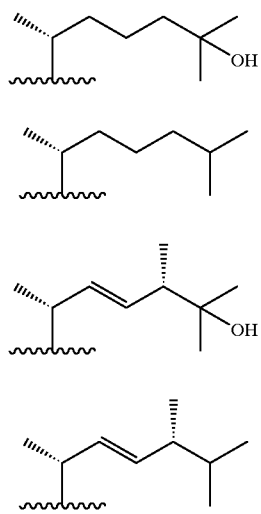

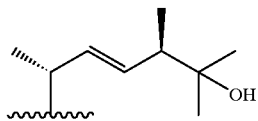

The above novel compounds exhibit a desired, and highly advantageous, pattern of biological activity. These compounds are characterized by little, if any intestinal calcium transport activity, as compared to that of 1α,25-dihydroxyvitamin D$_3$, while exhibiting relatively high activity, as compared to 1α,25-dihydroxyvitamin D$_3$, in their ability to mobilize calcium from bone. Hence, these compounds are highly specific in their calcemic activity. Their preferential activity on mobilizing calcium from bone and either low or normal intestinal calcium transport activity allows the in vivo administration of these compounds for the treatment of metabolic bone diseases where bone loss is a major concern. Because of their preferential calcemic activity on bone, these compounds would be preferred therapeutic agents for the treatment of diseases where bone formation is desired, such as osteoporosis, especially low bone turn-over osteoporosis, steroid induced osteoporosis, senile osteoporosis or postmenopausal osteoporosis, as well as osteomalacia and renal osteodystrophy. The treatment may be transdermal, oral or parenteral. The compounds may be present in a composition in an amount from about 0.1 µg/gm to about 50 µg/gm of the composition, and may be administered in dosages of from about 0.1 µg/day to about 50 µg/day.

The compounds of the invention are also especially suited for treatment and prophylaxis of human disorders which are characterized by an imbalance in the immune system, e.g. in autoimmune diseases, including multiple sclerosis, diabetes mellitus, host versus graft reaction, and rejection of transplants; and additionally for the treatment of inflammatory diseases, such as rheumatoid arthritis and asthma, as well as the improvement of bone fracture healing and improved bone grafts. Acne, alopecia, skin conditions such as dry skin (lack of dermal hydration), undue skin slackness (insufficient skin firmness), insufficient sebum secretion and wrinkles, and hypertension are other conditions which may be treated with the compounds of the invention.

The above compounds are also characterized by high cell differentiation activity. Thus, these compounds also provide therapeutic agents for the treatment of psoriasis, or as an anti-cancer agent, especially against leukemia, colon cancer, breast cancer and prostate cancer. The compounds may be present in a composition to treat psoriasis in an amount from about 0.01 µg/gm to about 100 µg/gm of the composition, and may be administered topically, transdermally, orally or parenterally in dosages of from about 0.01 µg/day to about 100 µg/day.

This invention also provides novel intermediate compounds formed during the synthesis of the end products.

This invention also provides a novel synthesis for the production of the end products of structure I.

DETAILED DESCRIPTION OF THE INVENTION

Figure 1:
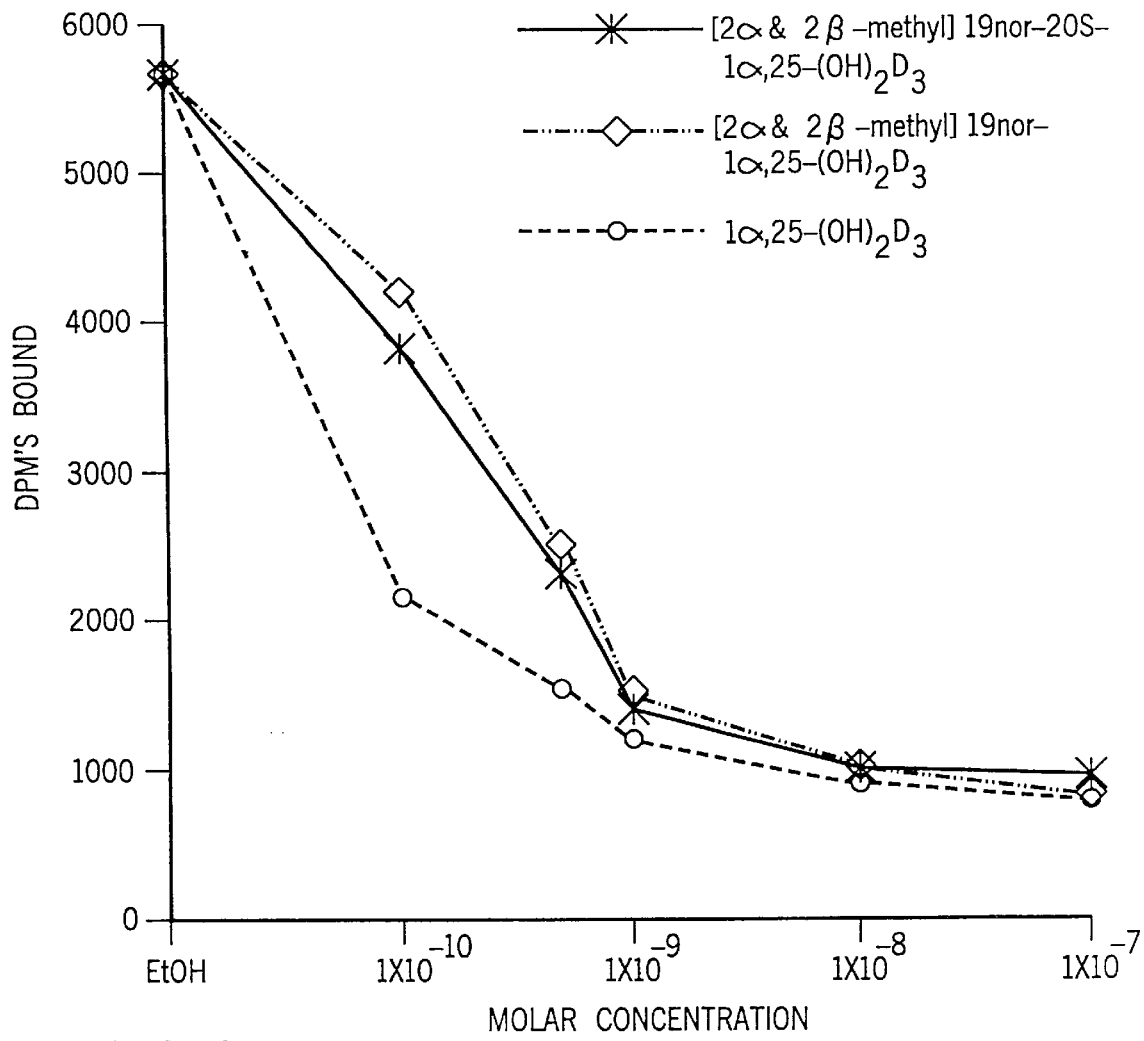
FIG. 1 is a graph illustrating the relative activity of a mixture of 2α and 2β-methyl-19-nor-20S-1,α25-dihydroxyvitamin D$_3$, a mixture of 2α and 2β-methyl-19-nor- 1α,25-dihydroxyvitamin D$_3$ and 1α,25-dihydroxyvitamin D$_3$ to compete for binding of [$^3$H]-1,25-(OH)$_2$-D$_3$ to the pig intestinal nuclear vitamin D receptor.

As used in the description and in the claims, the term "hydroxy-protecting group' signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

It should be noted in this description that the term "24-homo" refers to the addition of one methylene group and the term "24-dihomo" refers to the addition of two methylene groups at the carbon 24 position in the side chain. Likewise, the term "trihomo" refers to the addition of three methylene groups. Also, the term "26,27-dimethyl" refers to the addition of a methyl group at the carbon 26 and 27 positions so that for example $R^3$ and $R^4$ are ethyl groups. Likewise, the term "26,27-diethyl" refers to the addition of an ethyl group at the 26 and 27 positions so that $R^3$ and $R^4$ are propyl groups.

In the following lists of compounds, the particular substituent attached at the carbon 2 position should be added to the nomenclature. For example, if a methyl group is the alkyl substituent, the term "2-methyl" should precede each of the named compounds. If an ethyl group is the alkyl substituent, the term "2-ethyl" should precede each of the named compounds, and so on. In addition, if the methyl group attached at the carbon 20 position is in its epi or unnatural configuration, the term "20(S)" or "20-epi" should be included in each of the following named compounds. Also, if the side chain contains an oxygen atom substituted at any of positions 20, 22 or 23, the term "20-oxa", "22-oxa" or "23-oxa", respectively, should be added to the named compound. The named compounds could also be of the vitamin $D_2$ type if desired.

Specific and preferred examples of the 2-alkyl-compounds of structure I when the side chain is unsaturated are:

19-nor-24-homo-1,25-dihydroxy-22,23-dehydrovitamin $D_3$;

19-nor-24-dihomo-1,25-dihydroxy-22,23-dehydrovitamin $D_3$;

19-nor-24-trihomo-1,25-dihydroxy-22,23-dehydrovitamin $D_3$;

19-nor-26,27-dimethyl-24-homo-1,25-dihydroxy-22,23-dehydrovitamin $D_3$;

19-nor-26,27-dimethyl-24-dihomo-1,25-dihydroxy-22,23-dehydrovitamin $D_3$;

19-nor-26,27-dimethyl-24-trihomo-1,25-dihydroxy-22,23-dehydrovitamin $D_3$;

19-nor-26,27-diethyl-24-homo-1,25-dihydroxy-22,23-dehydrovitamin $D_3$;

19-nor-26,27-diethyl-24-dihomo-1,25-dihydroxy-22,23-dehydrovitamin $D_3$;

19-nor-26,27-diethyl-24-trihomo-1,25-dihydroxy-22,23-dehydrovitamin $D_3$;

19-nor-26,27-dipropoyl-24-homo-1,25-dihydroxy-22,23-dehydrovitamin $D_3$;

19-nor-26,27-dipropyl-24-dihomo-1,25-dihydroxy-22,23-dehydrovitamin $D_3$;

and 19-nor-26,27-dipropyl-24-trihomo-1,25-dihydroxy-22,23-dehydrovitamin $D_3$.

With respect to the above unsaturated compounds, it should be noted that the double bond located between the 22 and 23 carbon atoms in the side chain may be in either the (E) or (Z) configuration. Accordingly, depending upon the configuration, the term "22,23(E)" or "22,23(Z)" should be included in each of the above named compounds. Also, it is common to designate the double bond located between the 22 and 23 carbon atoms with the designation "$\Delta^{22}$". Thus, for example, the first named compound above could also be written as 19-nor-24-homo-22,23(E)-$\Delta^{22}$-1,25-$(OH)_2D_3$ where the double bond is in the (E) configuration. Similarly, if the methyl group attached at carbon 20 is in the unnatural configuration, this compound could be written as 19-nor-20(S)-24-homo-22,23(E)-$\Delta^{22}$-,1,25-$(OH)_2D_3$.

Specific and preferred examples of the 2-alkyl-compounds of structure I when the side chain is saturated are:

19-nor-24-homo-1,25-dihydroxyvitamin $D_3$;

19-nor-24-dihomo-1,25-dihydroxyvitamin $D_3$;

19-nor-24-trihomo-1,25-dihydroxyvitamin $D_3$;

19-nor-26,27-dimethyl-24-homo-1,25-dihydroxyvitamin $D_3$;

1 9-nor-26,27-dimethyl-24-dihomo-1,25-dihydroxyvitamin $D_3$;

19-nor-26,27-dimethyl-24-trihomo-1,25-dihydroxyvitamin $D_3$;

19-nor-26,27-diethyl-24-homo-1,25-dihydroxyvitamin $D_3$;

19-nor-26,27-diethyl-24-dihomo-1,25-dihydroxyvitamin $D_3$;

19-nor-26,27-diethyl-24-trihomo-1,25-dihydroxyvitamin $D_3$;

19-nor-26,27-dipropyl-24-homo-1,25-dihydroxyvitamin $D_3$;

19-nor-26,27-dipropyl-24-dihomo-1,25-dihydroxyvitamin $D_3$; and 19-nor-26,27-dipropyl-24-trihomo-1,25-dihydroxyvitamin $D_3$.

The preparation of 1α-hydroxy-2-alkyl-19-nor-vitamin D compounds, particularly 1α-hydroxy-2-methyl-19-nor-vitamin D compounds, having the basic structure I can be accomplished by a common general method, i.e. the condensation of a bicyclic Windaus-Grundmann type ketone II with the allylic phosphine oxide III to the corresponding 2-methylene-19-nor-vitamin D analogs IV followed by a selective reduction of the exomethylene group at C-2 in the latter compounds:

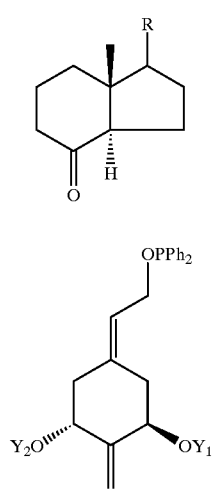

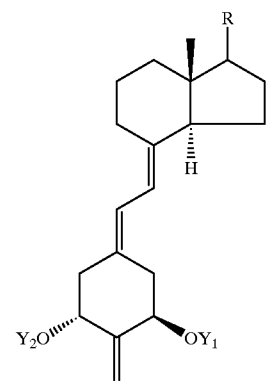

In the structures II, III, and IV groups $Y_1$ and $Y_2$ and R represent groups defined above; $Y_1$ and $Y_2$ are preferably hydroxy-protecting groups, it being also understood that any functionalities in R that might be sensitive, or that interfere with the condensation reaction, be suitable protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

Hydrindanones of the general structure II are known, or can be prepared by known methods. Specific important examples of such known bicyclic ketones are the structures with the side chains (a), (b), (c) and (d) described above, i.e. 25-hydroxy Grundmann's ketone (f) [Baggiolini et al., J. Org. Chem, 51, 3098 (1986)]; Grundmann's ketone (g) [Inhoffen et al., Chem. Ber. 90, 664 (1957)]; 25-hydroxy Windaus ketone (h) [Baggiolini et al., J. Org. Chem., 51, 3098 (1986)] and Windaus ketone (i) [Windaus et al., Ann., 524, 297 (1936)]:

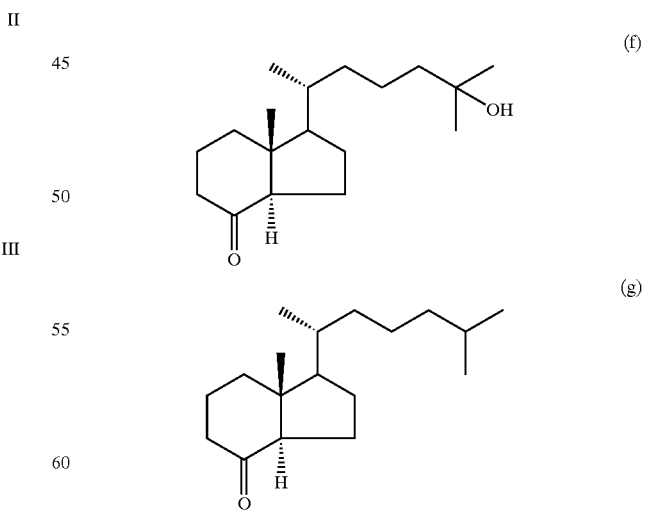

-continued

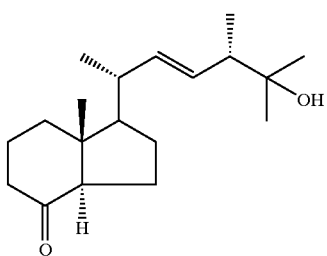

(h)

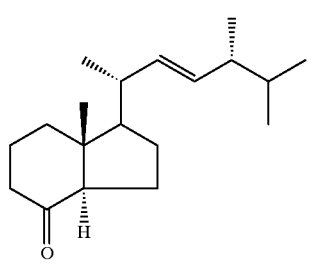

(i)

For the preparation of the required phosphine oxides of general structure III, a new synthetic route has been developed starting from methyl quinicate derivative 1, easily obtained from commercial (1R,3R,4S,5R)-(−)-quinic acid as described by Perlman et al., Tetrahedron Lett. 32, 7663 (1991) and DeLuca et al., U.S. Pat. No. 5,086,191. The overall process of transformation of the starting methyl ester 1 into the desired A-ring synthons, is summarized by the SCHEME I. Thus, the secondary 4-hydroxyl group of 1 was oxidized with $RuO_4$ (a catalytic method with $RuCl_3$ and $NaIO_4$ as co-oxidant). Use of such a strong oxidant was necessary for an effective oxidation process of this very hindered hydroxyl. However, other more commonly used oxidants can also be applied (e.g. pyridinium dichromate), although the reactions usually require much longer time for completion. Second step of the synthesis comprises the Wittig reaction of the sterically hindered 4-keto compound 2 with ylide prepared from methyltriphenylphosphonium bromide and n-butyllithium. Other bases can be also used for the generation of the reactive methylenephosphorane, like t-BuOK, $NaNH_2$, NaH, K/HMPT, $NaN(TMS)_2$, etc. For the preparation of the 4-methylene compound 3 some described modifications of the Wittig process can be used, e.g. reaction of 2 with activated methylenetriphenyl-phosphorane [Corey et al., Tetrahedron Lett. 26, 555 (1985)]. Alternatively, other methods widely used for methylenation of unreactive ketones can be applied, e.g. Wittig-Horner reaction with the PO-ylid obtained from methyldiphenylphosphine oxide upon deprotonation with n-butyllithium [Schosse et al., Chimia 30, 197 (1976)], or reaction of ketone with sodium methylsulfinate [Corey et al., J. Org. Chem. 28, 1128 (1963)] and potassium methylsulfinate [Greene et al., Tetrahedron Lett. 3755 (1976)]. Reduction of the ester 3 with lithium aluminum hydride or other suitable reducing agent (e.g. DIBALH) provided the diol 4 which was subsequently oxidized by sodium periodate to the cyclohexanone derivative 5. The next step of the process comprises the Peterson reaction of the ketone 5 with methyl(trimethylsilyl)acetate. The resulting allylic ester 6 was treated with diisobutylaluminum hydride and the formed allylic alcohol 7 was in turn transformed to the desired A-ring phosphine oxide 8. Conversion of 7 to 8 involved 3 steps, namely, in situ tosylation with n-butyllithium and p-toluenesulfonyl chloride, followed by reaction with diphenylphosphine lithium salt and oxidation with hydrogen peroxide.

Several 2-methylene-19-nor-vitamin D compounds of the general structure IV may be synthesized using the A-ring synthon 8 and the appropriate Windaus-Grundmann ketone II having the desired side chain structure. Thus, for example, Wittig-Horner coupling of the lithium phosphinoxy carbanion generated from 8 and n-butyllithium with the protected 25-hydroxy Grundmann's ketone 9 prepared according to published procedure [Sicinski et al., J. Med. Chem. 37, 3730 (1994)] gave the expected protected vitamin compound 10. This, after deprotection with AG 50W-X4 cation exchange resin afforded 1α,25-dihydroxy-2-methylene-19-nor-vitamin $D_3$ (11).

The final step of the process was the selective homogeneous catalytic hydrogenation of the exomethylene unit at carbon 2 in the vitamin 11 performed efficiently in the presence of tris(triphenylphosphine)rhodium(I) chloride [Wilkinson's catalyst, $(Ph_3P)_3RhCl$]. Such reduction conditions allowed to reduce only $C(2)=CH_2$ unit leaving C(5) –C(8) butadiene moiety unaffected. The isolated material is an epimeric mixture (ca. 1:1) of 2-methyl-19-nor-vitamins 12 and 13 differing in configuration at C-2. The mixture can be used without separation or, if desired, the individual 2α- and 2β-isomers can be separated by an efficient HPLC system.

A similar chemoselectivity was also observed in hydroboration reactions to synthesize 2-hydroxymethyl derivatives 20 and 21 (see Scheme III). For this purpose, 9-borabicyclo (3.3.1)nonane(9-BBN) was used as a reagent and reaction conditions analogous as those used by Okamura for hydroboration of simple vitamin D compounds. See J. Org. Chem. 1978, 43, 1653–1656 and J. Org. Chem. 1977, 42, 2284–2291. Since this literature precedent concerned hydroboration of 1-desoxy compounds, namely, (5E)- and (5Z)-isomers of vitamin $D_2$ and $D_3$, the process was first tested using 1α,25-$(OH)_2D_3$ as a model compound. The formed organoborane intermediate was subsequently oxidized with basic hydrogen peroxide. Such hydroboration-oxidation conditions allowed the exclusive hydroxylation of the $C(2)=CH_2$ unit in the vitamin 11, leaving the intercyclic C(5)=C(6)—C(7)=C(8) diene moiety unaffected. The isolated epimeric mixture of 2-hydroxymethyl derivatives 20 and 21 (ca. 1:2, 35% yield) was purified and separated by straight- and reversed-phase HPLC.

The C-20 epimerization was accomplished by the analogous coupling of the phosphine oxide 8 with protected (20S)-25-hydroxy Grundmann's ketone 15 (SCHEME II) and provided 19-nor-vitamin 16 which after hydrolysis of the hydroxy-protecting groups gave (20S)-1α,25-dihydroxy-2-methylene-19-nor-vitamin $D_3$ (17). Hydrogenation of 17 using Wilkinson's catalyst provided the expected mixture of the 2-methyl-19-nor-vitamin D analogs 18 and 19. Subsequent hydroboration with 9-BBN yielded (20S)-2-hydroxymethyl derivatives 22 and 23 (see Scheme III).

As noted above, other 2-methyl-19-nor-vitamin D analogs may be synthesized by the method disclosed herein. For example, 1α-hydroxy-2-methylene-19-nor-vitamin $D_3$ can be obtained by providing the Grundmann's ketone (g); subsequent reduction of the A-ring exomethylene group in the formed compound can give the corresponding epimeric mixture of 1α-hydroxy-2-methyl-19-nor-vitamin $D_3$ compounds.

A number of oxa-analogs of vitamin $D_3$ and their synthesis are also known. For example, 20-oxa analogs are described in N. Kubodera at al, Chem. Pharm. Bull., 34, 2286 (1986), and Abe et al, FEBS Lett. 222, 58, 1987. Several 22-oxa analogs are described in E. Murayama et al, Chem. Pharm. Bull., 34, 4410 (1986), Abe et al, FEBS Lett., 226, 58 (1987), PCT International Application No. WO 90/09991 and European Patent Application, publication number 184 112, and a 23-oxa analog is described in European Patent Application, publication number 78704, as well as U.S. Pat. No. 4,772,433.

This invention is described by the following illustrative examples. In these examples specific products identified by Arabic numerals (e.g. 1, 2, 3, etc) refer to the specific structures so identified in the preceding description and in the SCHEME I and SCHEME II.

EXAMPLE 1

Preparation of 1α,25-dihydroxy-2α- and 1α,25-dihydroxy-2β-methyl-19-nor-vitamin $D_3$ (12 and 13).

Referring first to SCHEME I the starting methyl quinicate derivative 1 was obtained from commercial (−)-quinic acid as described previously [Perlman et al., Tetrahedron Lett. 32, 7663 (1991) and DeLuca et al., U.S. Pat. No. 5,086,191]. 1: mp. 82–82.5° C. (from hexane), $^1$H NMR (CDCl$_3$) δ 0.098, 0.110, 0.142, and 0.159 (each 3H, each s, 4×SiCH$_3$), 0.896 and 0.911 (9H and 9H, each s, 2×Si-t-Bu), 1.820 (1H, dd, J=13.1, 10.3 Hz), 2.02 (1H, ddd, J=14.3,4.3, 2.4 Hz), 2.09 (1H, dd, J=14.3, 2.8 Hz), 2.19 (1H, ddd, J=13.1, 4.4, 2.4 Hz), 2.31 (1H, d, J=2.8 Hz, OH), 3.42 (1H, m; after D$_2$O dd, J=8.6, 2.6 Hz), 3.77 (3H, s), 4.12 (1H, m), 4.37 (1H, m), 4.53 (1H, br s, OH).

(a) Oxidation of 4-hydroxy group in methyl quinicate derivative 1.

(3 R,5R)-3,5-Bis[(tert-butyldimethylsilyl)oxy]-1-hydroxy-4-oxocyclohexanecarboxylic Acid Methyl Ester (2). To a stirred mixture of ruthenium(III) chloride hydrate (434 mg, 2.1 mmol) and sodium periodate (10.8 g, 50.6 mmol) in water (42 mL) was added a solution of methyl quinicate 1 (6.09 g, 14 mmol) in CCl$_4$/CH$_3$CN (1:1, 64 mL). Vigorous stirring was continued for 8 h. Few drops of 2-propanol were added, the mixture was poured into water and extracted with chloroform. The organic extracts were combined, washed with water, dried (MgSO$_4$) and evaporated to give a dark oily residue (ca. 5 g) which was purified by flash chromatography. Elution with hexane/ethyl acetate (8:2) gave pure, oily 4-ketone 2 (3.4 g, 56%): $^1$H NMR (CDCl$_3$) δ 0.054, 0.091, 0.127, and 0.132 (each 3H, each s, 4×SiCH$_3$), 0.908 and 0.913 (9H and 9H, each s, 2×Si-t-Bu), 2.22 (1H, dd, J=13.2, 11.7 Hz), 2.28 (1H, ~dt, J=14.9, 3.6 Hz), 2.37 (1H, dd, J=14.9, 3.2 Hz), 2.55 (1H, ddd, J=13.2, 6.4, 3.4 Hz), 3.79 (3H, s), 4.41 (1H, t, J~3.5 Hz), 4.64 (1H, s, OH), 5.04 (1H, dd, J=11.7, 6.4 Hz); MS m/z (relative intensity) no M$^+$, 375 (M$^+$-t-Bu, 32), 357 (M$^+$-t-Bu-H$_2$O, 47), 243 (31), 225 (57), 73 (100).

(b) Wittig reaction of the 4-ketone 2.

(3R,5R)-3,5-Bis[(tert-butyldimethylsilyl)oxy]-1-hydroxy-4-methylenecyclohexanecarboxylic Acid Methyl Ester (3). To the methyltriphenylphoshonium bromide (2.813 g, 7.88 mmol) in anhydrous THF (32 mL) at 0° C. was added dropwise n-BuLi (2.5 M in hexanes, 6.0 mL, 15 mmol) under argon with stirring. Another portion of MePh$_3$P$^+$Br$^-$ (2.813 g, 7.88 mmol) was then added and the solution was stirred at 0° C. for 10 min and at room temperature for 40 min. The orange-red mixture was again cooled to 0° C. and a solution of 4-ketone 2 (1.558 g, 3.6 mmol) in anhydrous THF (16+2 mL) was syphoned to reaction flask during 20 min. The reaction mixture was stirred at 0° C. for 1 h and at room temperature for 3 h. The mixture was then carefully poured into brine cont. 1% HCl and extracted with ethyl acetate and benzene. The combined organic extracts were washed with diluted NaHCO$_3$ and brine, dried (MgSO$_4$) and evaporated to give an orange oily residue (ca. 2.6 g) which was purified by flash chromatography. Elution with hexane/ethyl acetate (9:1) gave pure 4-methylene compound 3 as a colorless oil (368 mg, 24%): $^1$H NMR (CDCl$_3$) δ 0.078, 0.083, 0.092, and 0.115 (each 3H, each s, 4×SiCH$_3$), 0.889 and 0.920 (9H and 9H, each s, 2×Si-t-Bu), 1.811 (1H, dd, J=12.6, 11.2 Hz), 2.10 (2H, m), 2.31 (1H, dd, J=12.6,5.1 Hz), 3.76 (3H, s), 4.69 (1H, t, J=3.1 Hz), 4.78 (1H, m), 4.96 (2H, m; after D$_2$O 1H, br s), 5.17 (1H, t, J=1.9 Hz); MS m/z (relative intensity) no M$^+$, 373 (M$^+$-t-Bu, 57), 355 (M$^+$-t-Bu-H$_2$O, 13), 341 (19), 313 (25), 241 (33), 223 (37), 209 (56), 73 (100).

(c) Reduction of ester group in the 4-methylene compound 3.

[(3'R,5'R)-3',5'-Bis[(tert-butyldimethylsilyl)oxy]-1-hydroxy-4'-methylenecyclohexyl]methanol (4). (i) To a stirred solution of the ester 3 (90 mg, 0.21 mmol) in anhydrous THF (8 mL) lithium aluminum hydride (60 mg, 1.6 mmol) was added at 0° C. under argon. The cooling bath was removed after 1 h and the stirring was continued at 6° C. for 12 h and at room temperature for 6 h. The excess of the reagent was decomposed with saturated aq. Na$_2$SO$_4$, and the mixture was extracted with ethyl acetate and ether, dried (MgSO$_4$) and evaporated. Flash chromatography of the residue with hexane/ethyl acetate (9:1) afforded unreacted substrate (12 mg) and a pure, crystalline diol 4 (35 mg, 48% based on recovered ester 3): $^1$H NMR (CDCl$_3$+D$_2$O) δ 0.079, 0.091, 0.100, and 0.121 (each 3H, each s, 4×SiCH$_3$), 0.895 and 0.927 (9H and 9H, each s, 2×Si-t-Bu), 1.339 (1H, t, J~12 Hz), 1.510 (1H, dd, J=14.3,2.7 Hz), 2.10 (2H, m), 3.29 and 3.40 (1H and 1H, each d,J=1.0 Hz), 4.66 (1H, t, J~2.8 Hz), 4.78 (1H, m), 4.92 (1H, t, J=1.7 Hz), 5.13 (1H, t, J=2.0 Hz); MS m/z (relative intensity) no M$^+$, 345 (M$^+$-t-Bu, 8), 327 (M$^+$-t-Bu-H$_2$O, 22), 213 (28), 195 (11), 73 (100). (ii) Diisobutylaluminum hydride (1.5 M in toluene, 2.0 mL, 3 mmol) was added to a solution of the ester 3 (215 mg, 0.5 mmol) in anhydrous ether (3 mL) at −78° C. under argon. The mixture was stirred at −78° C. for 3 h and at −24° C. for 1.5 h, diluted with ether (10 mL) and quenched by the slow addition of 2N potassium sodium tartrate. The solution was warmed to room temperature and stirred for 15 min, then poured into brine and extracted with ethyl acetate and ether.

The organic extracts were combined, washed with diluted (ca. 1%) HCl, and brine, dried (MgSO$_4$) and evaporated. The crystalline residue was purified by flash chromatography. Elution with hexane/ethyl acetate (9:1) gave crystalline diol 4 (43 mg, 24%).

(d) Cleavage of the vicinal diol 4.

(3R,5R)-3,5-Bis[(tert-butyldimethylsilyl)oxy]-4-methylenecyclohexanone (5). Sodium periodate saturated water (2.2 mL) was added to a solution of the diol 4 (146 mg, 0.36 mmol) in methanol (9 mL) at 0° C. The solution was stirred at 0° C. for 1 h, poured into brine and extracted with ether and benzene. The organic extracts were combined, washed with brine, dried (MgSO$_4$) and evaporated. An oily residue was dissolved in hexane (1 mL) and applied on a silica Sep-Pak cartridge. Pure 4-methylenecyclohexanone derivative 5 (110 mg, 82%) was eluted with hexane/ethyl acetate (95:5) as a colorless oil: $^1$H NMR (CDCl$_3$) δ 0.050 and 0.069 (6H and 6H, each s, 4×SiCH$_3$), 0.881 (18H, s, 2×Si-t-Bu), 2.45 (2H, ddd, J=14.2, 6.9, 1.4 Hz), 2.64 (2H, ddd, J=14.2, 4.6, 1.4 Hz), 4.69 (2H, dd, J=6.9, 4.6 Hz), 5.16 (2H, s); MS m/z (relative intensity) no M$^+$, 355 (M$^+$-Me, 3), 313 (M$^+$-t-Bu, 100), 73 (76).

(e) Preparation of the allylic ester 6.

[(3 'R,5'R)-3',5'-Bis[(tert-butyldimethylsilyl)oxy]-4'-methylenecyclohexylidene]acetic Acid Methyl Ester (6). To a solution of diisopropylamine (37 μL, 0.28 mmol) in anhydrous THF (200 μL) was added n-BuLi (2.5 M in hexanes, 113 μL, 0.28 mmol) under argon at −78° C. with stirring, and methyl(trimethylsilyl)acetate (46 μL, 0.28 mmol) was then added. After 15 min, the keto compound 5 (49 mg, 0.132 mmol) in anhydrous THF (200+80 μL) was added dropwise. The solution was stirred at −78° C. for 2 h and the reaction mixture was quenched with saturated $NH_4Cl$, poured into brine and extracted with ether and benzene. The combined organic extracts were washed with brine, dried ($MgSO_4$) and evaporated. The residue was dissolved in hexane (1 mL) and applied on a silica Sep-Pak cartridge. Elution with hexane and hexane/ethyl acetate (98:2) gave a pure allylic ester 6 (50 mg, 89%) as a colorless oil: $^1$H NMR ($CDCl_3$) δ 0.039, 0.064, and 0.076 (6H, 3H, and 3H, each s, 4×$SiCH_3$), 0.864 and 0.884 (9H and 9H, each s, 2×Si-t-Bu), 2.26 (1H, dd, J=12.8, 7.4 Hz), 2.47 (1H, dd, J=12.8, 4.2 Hz), 2.98 (1H, dd, J=13.3, 4.0 Hz), 3.06 (1H, dd, J=13.3, 6.6 Hz), 3.69 (3H, s), 4.48 (2H, m), 4.99 (2H, s), 5.74 (1H, s); MS m/z (relative intensity) 426 ($M^+$, 2), 411 ($M^+$-Me, 4), 369 ($M^+$-t-Bu, 100), 263 (69).

(f) Reduction of the allylic ester 6.

2-[(3'R,5'R)-3',5'-Bis[(tert-butyldimethylsilyl)oxy]-4'-methylenecyclohexylidene]ethanol (7). Diisobutylaluminum hydride (1.5 M in toluene, 1.6 mL, 2.4 mmol) was slowly added to a stirred solution of the allylic ester 6 (143 mg, 0.33 mmol) in toluene/methylene chloride (2:1, 5.7 mL) at −78° C. under argon. Stirring was continued at −78° C. for 1 h and at −46° C. (cyclohexanone/dry ice bath) for 25 min. The mixture was quenched by the slow addition of potassium sodium tartrate (2N, 3 mL), aq. HCl (2N, 3 mL) and $H_2O$ (12 mL), and then diluted with methylene chloride (12 mL) and extracted with ether and benzene. The organic extracts were combined, washed with diluted (ca. 1%) HCl, and brine, dried ($MgSO_4$) and evaporated. The residue was purified by flash chromatography. Elution with hexane/ethyl acetate (9:1) gave crystalline allylic alcohol 7 (130 mg, 97%): $^1$H NMR ($CDCl_3$) δ 0.038, 0.050, and 0.075 (3H, 3H, and 6H, each s, 4×$SiCH_3$), 0.876 and 0.904 (9H and 9H, each s, 2×Si-t-Bu), 2.12 (1H, dd, J=12.3, 8.8 Hz), 2.23 (1H, dd, J=13.3, 2.7 Hz), 2.45 (1H, dd, J=12.3, 4.8 Hz), 2.51 (1H, dd, J=13.3, 5.4 Hz), 4.04 (1H, m; after $D_2O$ dd, J=12.0, 7.0 Hz), 4.17 (1H, m; after $D_2O$ dd, J=12.0, 7.4 Hz), 4.38 (1H, m), 4.49 (1H, m), 4.95 (1H, br s), 5.05 (1H, t, J=1.7 Hz), 5.69 (1H, ~t, J=7.2 Hz); MS m/z (relative intensity) 398 ($M^+$, 2), 383 ($M^+$-Me, 2), 365 ($M^+$-Me -$H_2O$, 4), 341 ($M^+$-t-Bu, 78), 323 ($M^+$-t-Bu-$H_2O$, 10), 73 (100); exact mass calcd for $C_{27}H_{44}O_3$ 416.3290, found 416.3279.

(g) Conversion of the allylic alcohol 7 into phosphine oxide 8.

[2-[(3'R,5'R)-3',5'-Bis[(tert-butyldimethylsilyl)oxy]-4'-methylenecyclohexylidene]ethyl]diphenylphosphine Oxide (8). To the allylic alcohol 7 (105 mg, 0.263 mmol) in anhydrous THF (2.4 mL) was added n-BuLi (2.5 M in hexanes, 105 μL, 0.263 mmol) under argon at 0° C. Freshly recrystallized tosyl chloride (50.4 mg, 0.264 mmol) was dissolved in anhydrous THF (480 μL)and added to the allylic alcohol-BuLi solution . The mixture was stirred at 0° C. for 5 min and set aside at 0° C. In another dry flask with air replaced by argon, n-BuLi (2.5 M in hexanes, 210 μL, 0.525 mmol) was added to $Ph_2PH$ (93 μL, 0.534 mmol) in anhydrous THF (750 μL) at 0° C. with stirring. The red solution was syphoned under argon pressure to the solution of tosylate until the orange color persisted (ca. ½ of the solution was added). The resulting mixture was stirred an additional 30 min at 0° C., and quenched by addition of $H_2O$ (30 μl). Solvents were evaporated under reduced pressure and the residue was redissolved in methylene chloride (2.4 mL) and stirred with 10% $H_2O_2$ at 0° C. for 1 h. The organic layer was separated, washed with cold aq. sodium sulfite and $H_2O$, dried ($MgSO_4$) and evaporated. The residue was subjected to flash chromatography. Elution with benzene/ethyl acetate (6:4) gave semicrystalline phosphine oxide 8 (134 mg, 87%): $^1$H NMR ($CDCl_3$) δ 0.002, 0.011, and 0.019 (3H, 3H, and 6H, each s, 4×$SiCH_3$), 0.855 and 0.860 (9H and 9H, each s, 2×Si-t-Bu), 2.0–2.1 (3H, br m), 2.34 (1H, m), 3.08 (1H, m), 3.19 (1H, m), 4.34 (2H, m), 4.90 and 4.94 (1H and 1H, each s,), 5.35 (1H, ~q, J=7.4 Hz), 7.46 (4H, m), 7.52 (2H, m), 7.72 (4H, m); MS m/z (relative intensity) no $M^+$, 581 ($M^+$-1, 1), 567 ($M^+$-Me, 3), 525 ($M^+$-t-Bu, 100), 450 (10), 393 (48).

(h) Wittig-Horner coupling of protected 25-hydroxy Grundmann's ketone 9 with the phosphine oxide 8.

1α,25-Dihydroxy-2-methylene-19-nor-vitamin $D_3$ (11). To a solution of phosphine oxide 8 (33.1 mg, 56.8 mmol) in anhydrous THF (450 μL) at 0° C. was slowly added n-BuLi (2.5 M in hexanes, 23 μL, 57.5 μmol) under argon with stirring. The solution turned deep orange. The mixture was cooled to −78° C. and a precooled (−78° C.) solution of protected hydroxy ketone 9 (9.0 mg, 22.8 μmol), prepared according to published procedure [Sicinski et al., J. Med. Chem. 37, 3730 (1994)], in anhydrous THF (200+100 μL) was slowly added. The mixture was stirred under argon at−78° C. for 1 h and at 0° C. for 18 h. Ethyl acetate was added, and the organic phase was washed with brine, dried ($MgSO_4$) and evaporated. The residue was dissolved in hexane and applied on a silica Sep-Pak cartridge, and washed with hexane/ethyl acetate (99:1, 20 mL) to give 19-nor-vitamin derivative 10 (13.5 mg, 78%). The Sep-Pak was then washed with hexane/ethyl acetate (96:4, 10 mL) to recover some unchanged C,D-ring ketone 9 (2 mg), and with ethyl acetate (10 mL) to recover diphenylphosphine oxide (20 mg). For analytical purpose a sample of protected vitamin 10 was further purified by HPLC (6.2 mm×25 cm Zorbax-Sil column, 4 mL/min) using hexane/ethyl acetate (99.9:0.1) solvent system. Pure compound 10 was eluted at Rv 26 mL as a colorless oil: UV (in hexane) λmax 244, 253, 263 nm; $^1$H NMR ($CDCl_3$) δ 0.025, 0.049, 0.066, and 0.080 (each 3H, each s, 4×$SiCH_3$), 0.546 (3H, s, 18-$H_3$), 0.565 (6H, q, J=7.9 Hz, 3×$SiCH_2$), 0.864 and 0.896 (9H and 9H, each s, 2×Si-t-Bu), 0.931 (3H, d, J=6.0 Hz, 21-$H_3$), 0.947 (9H, t, J=7.9 Hz, 3×$SiCH_2CH_3$), 1.188 (6H, s, 26- and 27-$H_3$), 2.00 (2H, m), 2.18 (1H, dd, J=12.5, 8.5 Hz, 4β-H), 2.33 (1H, dd, J=13.1, 2.9 Hz, 10β-H), 2.46 (1H, dd, J=12.5, 4.5 Hz, 4α-H), 2.52 (1H, dd, J=13.1, 5.8 Hz, 10α-H), 2.82 (1H, br d, J=12 Hz, 9β-H), 4.43 (2H, m, 1β- and 3α-H), 4.92 and 4.97 (1H and 1H, each s, =$CH_2$), 5.84 and 6.22 (1H and 1H, each d, J=11.0 Hz, 7- and 6-H); MS m/z (relative intensity) 758 ($M^+$, 17), 729 ($M^+$-Et, 6), 701 ($M^+$-t-Bu, 4), 626 (100), 494 (23), 366 (50), 73 (92).

Protected vitamin 10 (4.3 mg) was dissolved in benzene (150 μL) and the resin (AG 50W-X4, 60 mg; prewashed with methanol) in methanol (800 μL) was added. The mixture was stirred at room temperature under argon for 17 h, diluted with ethyl acetate/ether (1:1, 4 mL) and decanted. The resin was washed with ether (8 mL) and the combined organic phases washed with brine and saturated $NaHCO_3$, dried ($MgSO_4$) and evaporated. The residue was purified by HPLC (6.2 mm×25 cm Zorbax-Sil column, 4 mL/min) using hexane/2-propanol (9:1) solvent system. Analytically pure 2-methylene-19-nor-vitamin 11 (2.3 mg, 97%) was collected at $R_v$ 29 mL (1α,25-dihydroxyvitamin $D_3$ was eluted at $R_v$ 52 mL in the same system) as a white solid: UV (in EtOH) $\lambda_{max}$ 243.5, 252, 262.5 nm; $^1$H NMR ($CDCl_3$) δ 0.552 (3H, s, 18-H$_3$), 0.941 (3H, d, J=6.4 Hz, 21-H$_3$), 1.222 (6H, s, 26- and 27-H$_3$), 2.01 (2H, m), 2.27–2.36 (2H, m), 2.58 (1H, m), 2.80–2.88 (2H, m), 4.49 (2H, m, 1β- and 3α-H), 5.10 and 5.11 (1H and 1H, each s, =CH$_2$), 5.89 and 6.37 (1H and 1H, each d, J=11.3 Hz, 7- and 6-H); MS m/z (relative intensity) 416 (M$^+$, 83), 398 (25), 384 (31), 380 (14), 351 (20), 313 (100); exact mass calcd for C$_{27}$H$_{44}$O$_3$ 416.3290, found 416.3279.

(i) Hydrogenation of 2-methylene-19-nor-vitamin 11.

1α,25-Dihydroxy-2α- and 1α,25-Dihydroxy-2β-methyl-19-nor-vitamin D$_3$ (12 and 13). Tris(triphenylphosphine)rhodium(I) chloride (2.3 mg, 2.5 μmol) was added to dry benzene (2.5 mL) presaturated with hydrogen. The mixture was stirred at room temperature until a homogeneous solution was formed (ca. 45 min). A solution of vitamin 11 (1.0 mg, 2.4 μmol) in dry benzene (0.5 mL) was then added and the reaction was allowed to proceed under a continuous stream of hydrogen for 3 h. Benzene was removed under vacuum, and hexane/ethyl acetate (1:1, 2 mL) was added to the residue. The mixture was applied on a silica Sep-Pak and both 2-methyl vitamins were eluted with the same solvent system (20 mL). Further purification was achieved by HPLC (6.2 mm×25 cm Zorbax-Sil column, 4 mL/min) using hexane/2-propanol (9: 1) as a solvent system. The mixture (ca. 1:1) of 2-methyl-1 9-nor-vitamins (2α- and 2β-epimers 12 and 13; 0.80 mg, 80%) gave a single peak at R$_v$ 33 mL.

12 and 13: UV (in EtOH) λ$_{max}$ 243, 251, 261.5 nm; $^1$H NMR (CDCl$_3$) δ 0.536 and 0.548 (3H and 3H, each s, 2×18-H$_3$), 0.937 (6H, d, J=6.3 Hz, 2×21-H$_3$), 1.133 and 1.144 (3H and 3H, each d, J~6 Hz, 2×2—CH$_3$), 1.219 [12H, s, 2×(26- and 27-H$_3$)], 2.60 (1H, dd, J=13.0, 4.6 Hz), 2.80 (3H, m), 3.08 (1H, dd, J=12.6, 4.0 Hz), 3.51 (1H, dt, J=4.6, 10.2 Hz), 3.61 (1H, dt, J=4.5, 9.1 Hz), 3.90 (1H, narr m), 3.96 (1H, narr m), 5.82, 5.87, 6.26, and 6.37 (each 1H, each d, J=11.2 Hz); MS m/z (relative intensity) 418 (M$^+$, 100), 400 (25), 385 (15), 289 (30), 245 (25).

Separation of both epimers was achieved by reversed-phase HPLC (10 mm×25 cm Zorbax-ODS column, 4 mL/min) using methanol/water (85:15) solvent system. 2β-Methyl vitamin 13 (0.35 mg, 35%) was collected at R$_v$ 41 mL and its 2α-epimer 12 (0.34 mg, 34%) at R$_v$ 46 mL.

12: UV (in EtOH) λ$_{max}$ 243, 251, 261 nm; $^1$H NMR (CDCl$_3$) δ 0.536 (3H, s, 18-H$_3$), 0.937 (3H, d, J=6.4 Hz, 21-H$_3$), 1.134 (3H, d, J=6.9 Hz, 2α-CH$_3$), 1.218 (6H, s, 26- and 27-H$_3$), 2.13 (1H, ~t, J~12 Hz, 4β-H), 2.22 (1H, br d, J=13 Hz, 10β-H), 2.60 (1H, dd, J=12.8, 4.3 Hz, 4α-H), 2.80 (2H, m, 9β- and 10α-H), 3.61 (1H, m, w/2=24 Hz, 3α-H), 3.96 (1H, m, w/2=12 Hz, 1 β-H), 5.82 and 6.37 (1H and 1H, each d, J=11.1 Hz, 7-and 6-H); MS m/z (relative intensity) 418 (M$^+$, 62), 400 (32), 385 (17), 289 (36), 271 (17), 253 (20), 245 (43), 69 (100), 59 (74) ); exact mass calcd for C$_{27}$H$_{46}$O$_3$ 418.3447, found 25 418.3441.

13: UV (in EtOH) λ$_{max}$ 242, 250.5, 261 nm; $^1$H NMR (CDCl$_3$) δ 0.548 (3H, s, 18-$_3$), 0.940 (3H, d, J=6.4 Hz, 21-H$_3$), 1.143 (3H, d, J=6.8 Hz, 2β—CH$_3$), 1.220 (6H, s, 26- and 27-H$_3$), 2.34 (1H, dd, J 13.7, 3.3 Hz, 4β-H), 2.43 (1H, br d,J=13.7 Hz, 4α-H), 2.80 (1H, dd, J=12 and 4 Hz, 9β-H), 3.08 (1H, dd, J=13.0,4.2 Hz, 10β-H), 3.51 (1H, m, w/2=25 Hz, 1β-H), 3.90 (1H, m, w/2=11 Hz, 3α-H), 5.87 and 6.26 (1H and 1H, each d, J=11.2 Hz, 7- and 6-H); MS m/z (relative intensity) 418 (M$^+$, 63), 400 (47), 385 (16), 289 (40), 271 (32), 253 (27), 245 (47), 69 (100), 59 (64); exact mass calcd for C$_{27}$H$_{46}$O$_3$ 418.3447, found 418.3436.

EXAMPLE 2

Preparation of (20S)-1α,25-dihydroxy-2α- and (20S)-1α,25-dihydroxy-2β-methyl-19-nor-vitamin D$_3$ (18 and 19).

SCHEME II illustrates the preparation of protected (20S)-25-hydroxy Grundmann's ketone 15, its coupling with phosphine oxide 8 (obtained as described in Example 1) and selective hydrogenation of exomethylene group in 2-methylene compound 17.

(a) Silylation of hydroxy ketone 14.

(20S)-25-[(Triethylsilyl)oxy]-des-A,B-cholestan-8-one (15). A solution of the ketone 14 (Tetrionics, Inc.; 56 mg, 0.2 mmol) and imidazole (65 mg, 0.95 mmol) in anhydrous DMF (1.2 mL) was treated with triethylsilyl chloride (95 μL, 0.56 mmol), and the mixture was stirred at room temperature under argon for 4 h. Ethyl acetate was added and water, and the organic layer was separated. The ethyl acetate layer was washed with water and brine, dried (MgSO$_4$) and evaporated. The residue was passed through a silica Sep-Pak cartridge in hexane/ethyl acetate (9: 1), and after evaporation, purified by HPLC (9.4 mm×25 cm Zorbax-Sil column, 4 mL/min) using hexane/ethyl acetate (9:1) solvent system. Pure protected hydroxy ketone 15 (55 mg, 70%) was eluted at R$_v$ 35 mL as a colorless oil: $^1$H NMR (CDCl$_3$) δ 0.566 (6H, q, J=7.9 Hz, 3×SiCH$_2$), 0.638 (3H, s, 18-H$_3$), 0.859 (3H, d, J=6.0 Hz, 21-H$_3$), 0.947 (9H, t, J=7.9 Hz, 3×SiCH$_2$CH$_3$), 1.196 (6H, s, 26- and 27-H$_3$), 2.45 (1H, dd, J=11.4, 7.5 Hz, 14α-H).

(b) Wittig-Horner coupling of protected (20S)-25-hydroxy Grundmann's ketone 15 with the phosphine oxide 8.

(20S)-1α,25-Dihydroxy-2-methylene-19-nor-vitamin D$_3$ (17). To a solution of phosphine oxide 8 (15.8 mg, 27.1 μmol) in anhydrous THF (200 μL) at 0° C. was slowly added n-BuLi (2.5 M in hexanes, 11 μL, 27.5 μmol) under argon with stirring. The solution turned deep orange. The mixture was cooled to–78° C. and a precooled (–78° C.) solution of protected hydroxy ketone 15 (8.0 mg, 20.3 μmol) in anhydrous THF (100 μL) was slowly added. The mixture was stirred under argon at –78° C. for 1 h and at 0° C. for 18 h. Ethyl acetate was added, and the organic phase was washed with brine, dried (MgSO$_4$) and evaporated. The residue was dissolved in hexane and applied on a silica Sep-Pak cartridge, and washed with hexane/ethyl acetate (99.5:0.5, 20 mL) to give 19-nor-vitamin derivative 16 (7 mg, 45%) as a colorless oil. The Sep-Pak was then washed with hexane/ethyl acetate (96:4, 10 mL) to recover some unchanged C,D-ring ketone 15 (4 mg), and with ethyl acetate (10 mL) to recover diphenylphosphine oxide (9 mg). For analytical purpose a sample of protected vitamin 16 was further purified by HPLC (6.2 mm×25 cm Zorbax-Sil column, 4 mL/min) using hexane/ethyl acetate (99.9:0.1) solvent system.

16: UV (in hexane) λ$_{max}$ 244, 253.5, 263 nm; $^1$H NMR (CDCl$_3$) δ 0.026, 0.049, 0.066, and 0.080 (each 3H, each s, 4×SiCH$_3$), 0.541 (3H, s, 18-H$_3$), 0.564 (6H, q, J=7.9 Hz, 3×SiCH$_2$), 0.848 (3H, d, J=6.5 Hz, 21-H$_3$), 0.864 and 0.896 (9H and 9H, each s, 2×Si-t-Bu), 0.945 (9H, t, J=7.9 Hz, 3×SiCH$_2$CH$_3$), 1.188 (6H, s, 26- and 27-H$_3$), 2.15–2.35 (4H, br m), 2.43–2.53 (3H, br m), 2.82 (1H, br d, J=12.9 Hz, 9β-H), 4.42 (2H, m, 1α- and 3β-H), 4.92 and 4.97 (1H and 1H, each s, =CH$_2$), 5.84 and 6.22 (1H and 1H, each d, J=11.1 Hz, 7- and 6-H); MS rn/z (relative intensity) 758 (M$^+$, 33), 729 (M$^+$-Et, 7), 701 (M-t-Bu, 5), 626 (100), 494 (25), 366 (52), 75 (82), 73 (69).

Protected vitamin 16 (5.0 mg) was dissolved in benzene (160 μL) and the resin (AG 50W-X4, 70 mg; prewashed with methanol) in methanol (900 μL) was added. The mixture was stirred at room temperature under argon for 19 h, diluted with ethyl acetate/ether (1:1, 4 mL) and decanted. The resin was washed with ether (8 mL) and the combined organic phases washed with brine and saturated $NaHCO_3$, dried ($MgSO_4$) and evaporated. The residue was purified by HPLC (6.2 mm×25 cm Zorbax-Sil column, 4 mL/min) using hexane/2-propanol (9:1) solvent system. Analytically pure 2-methylene-19-nor-vitamin 17 (2.6 mg, 95%) was collected at $R_v$ 28 mL [(20R)-analog was eluted at $R_v$ 29 mL and 1α,25-dihydroxyvitamin $D_3$ at $R_v$ 52 mL in the same system] as a white solid: UV (in EtOH) $\lambda_{max}$ 243.5, 252.5, 262.5 nm; $^1$H NMR ($CDCl_3$) δ 0.551 (3H, s, 18-$H_3$), 0.858 (3H, d, J=6.6 Hz, 21-$H_3$), 1.215 (6H, s, 26- and 27-$H_3$), 1.95–2.04 (2H, m), 2.27–2.35 (2H, m), 2.58 (1H, dd, J=13.3, 3.7 Hz), 2.80–2.87 (2H, m), 4.49 (2H, m, 1α- and 3β-H), 5.09 and 5.11 (1 H and 1 H, each s, =$CH_2$), 5.89 and 6.36 (1 H and 1H, each d, J=11.3 Hz, 7- and 6-H); MS m/z (relative intensity) 416 ($M^+$, 100), 398 (26), 380 (13), 366 (21), 313 (31); exact mass calcd for $C_{27}H_{44}O_3$ 416.3290, found 416.3275.

(c) Hydrogenation of 2-methylene-1 9-nor-vitamin 17.

(20S)-1α,25-Dihydroxy-2α- and (20S)-1α,25-Dihydroxy-2β-methyl-19-nor-vitamin $D_3$ (18 and 19). Tris(triphenylphosphine)rhodium(I) chloride (2.3 mg, 2.5 μmol) was added to dry benzene (2.5 mL) presaturated with hydrogen. The mixture was stirred at room temperature until a homogeneous solution was formed (ca. 45 min). A solution of vitamin 17 (1.0 mg, 2.4 μmol) in dry benzene (0.5 mL) was then added and the reaction was allowed to proceed under a continuous stream of hydrogen for 3 h. Benzene was removed under vacuum, and hexane/ethyl acetate (1:1, 2 mL) was added to the residue.

The mixture was applied on a silica Sep-Pak and both 2-methyl vitamins were eluted with the same solvent system (20 mL). Further purification was achieved by HPLC (6.2 mm×25 cm Zorbax-Sil column, 4 mL/min) using hexane/2-propanol (9:1) as a solvent system. The mixture (ca. 1:1) of 2-methyl-19-nor-vitamins (2α- and 2β-epimers 18 and 19; 0.43 mg, 43%) gave a single peak at $R_v$ 31 mL.

18 and 19: UV (in EtOH) $\lambda_{max}$ 243, 251, 261 nm; $^1$H NMR ($CDCl_3$) δ 0.534 and 0.546 (3H and 3H, each s, 2×18-$H_3$), 0.852 and 0.857 (3H and 3H, each d, J=6.5 Hz, 2×21-$H_3$), 1.133 (3H, d, J=6.7 Hz, 2-$CH_3$), 1.143 (3H, d, J=6.5 Hz, 2-$CH_3$), 1.214 [12H, s, 2×(26- and 27-$H_3$)], 2.60 (1H, dd, J=12.7, 4.5 Hz), 2.80 (3H, m), 3.08 (1H, dd, J=13.1, 4.3 Hz), 3.51 (1H, br m; after $D_2O$ dt, J=4.5, 10.0 Hz), 3.61 (1H, br m; after $D_2O$ dt, J=4.4, 9.2 Hz), 3.90 (1H, narr m), 3.96 (1H, narr m), 5.82, 5.87, 6.26, and 6.37 (each 1H, each d, J=11.3 Hz); MS m/z (relative intensity) 418 ($M^+$, 100), 400 (45), 385 (20), 289 (38), 245 (47).

Separation of both epimers was achieved by reversed-phase HPLC (10 mm×25 cm Zorbax-ODS column, 4 mL/min) using methanol/water (85:15) solvent system. 2β-Methyl vitamin 19 (16%) was collected at $R_v$ 36 mL and its 2(x-epimer 18 (20%) at $R_v$ 45 mL.

18: UV (in EtOH) $\lambda_{max}$ 242.5, 251, 261 nm; $^1$H NMR ($CDCl_3$) δ 0.534 (3H, s, 18-$H_3$), 0.852 (3H, d, J=6.6 Hz, 21-$H_3$), 1.133 (3H, d, J=6.9 Hz, 2α—$CH_3$), 1.214 (6H, s, 26- and 27-$H_3$), 2.13 (1H, ~t, J~12 Hz, 4β-H), 2.22 (1H, br d, J=13 Hz, 10β-H), 2.60 (1H, dd, J=12.8, 4.4 Hz, 4α-H), 2.80 (2H, m, 9β- and 10α-H), 3.61 (1H, m, w/2=25 Hz, 3α-H), 3.95(1H, m, w/2=11 Hz, 1β-H), 5.82 and 6.37 (1H and 1H, each d, J=11.2 Hz, 7- and 6-H); MS m/z (relative intensity) 418 ($M^+$, 58), 400 (25), 385 (20), 289 (28), 271 (23). 253 (22), 245 (38), 69 (100), 59 (47) ); exact mass calcd for $C_{27}H_{46}O_3$ 418.3447, found 418.3450.

19: UV (in EtOH) $\lambda_{max}$ 242.5, 250.5, 261 nm; $^1$H NMR ($CDCl_3$) δ 0.547 (3H, s, 18-$H_3$), 0.857 (3H, d, J=6.6 Hz, 21-1$H_3$), 1.143 (3H, d, J=6.8 Hz, 2β—$CH_3$), 1.214 (6H, s, 26- and 27-$H_3$), 2.34 (1H, dd, J=13.8, 3.1 Hz, 4β-H), 2.43 (1H, br d, J=13.8 Hz, 4α-H), 2.80 (1H, dd, J=12 and 4 Hz, 9β-H), 3.08 (1H, dd, J=12.9, 4.4 Hz, 10β-H), 3.50 (1H, m, w/2=26 Hz, 1β-H), 3.89 (1H, m, w/2=11 Hz, 3α-H), 5.86 and 6.26 (1H and 1H, each d, J=11.2 Hz, 7- and 6-H); MS m/z (relative intensity) 418 ($M^+$, 68), 400 (47), 385 (21), 289 (33), 271 (27), 253 (26), 245 (47), 69 (100), 59 (53); exact mass calcd for $C_{27}H_{46}O_3$ 18.3447, found 418.3448.

1α,25-Dihydroxy-2α- and 1α,25-Dihydroxy-2β-(hydroxymethyl)-19-norvitamin $D_3$ (20 and 21). 9-Borabicyclo[3.3.1]nonane (0.5 M in THF, 60 μL, 30 μmol) was added to a solution of vitamin 11 (1.25 mg, 3 μmol) in anhydrous THF (50 μL) at room temperature (evolution of hydrogen was observed). After 3 h of stirring, the mixture was quenched with methanol (20 μL), stirred for 15 min at room temperature, cooled to 0° C., and treated successively with 6 M NaOH (10 μL, 60 μmol) and 30% $H_2O_2$ (10 μL). The mixture was heated for 1 h at 55° C., cooled, benzene and brine were added, and the organic phase was separated, dried and evaporated. The crystalline residue was dissolved in ether (0.5 mL) and kept in freezer overnight. The ether solution was carefully removed from the precipitated crystals of cyclooctanediol and evaporated. Separation of the residue was achieved by HPLC (6.2 mm×25 cm Zorbax-Sil column, 4 mL/min) using hexane/2-propanol (85:15) solvent system. Traces of unreacted substrate 11 were eluted at $R_v$ 16 mL, whereas isomeric 2-hydroxymethyl vitamins 20 and 21 were collected at $R_v$ 33 mL and 40 mL, respectively. Further purification of both products by reversed-phase HPLC (10 mm×25 cm Zorbax-ODS column, 4 mL/min) using methanol/water (9:1) solvent system afforded analytically pure vitamin 20 (0.14 mg, 11%) and its 2β-isomer 21 (0.31 mg, 24%) collected at $R_v$ 26 mL and 23 mL, respectively.

20: UV (in EtOH) $\lambda_{max}$ 242.5, 250.5, 261 nm; $^1$H NMR ($CDCl_3$) δ 0.536 (3H, s, 18-$H_3$), 0.939 (3H, d, J=6.4 Hz, 21-$H_3$), 1.214 (6H, s, 26- and 27-$H_3$), 2.13 (1H, br d, J=13.5 Hz, 10β-H), 2.21 (1H, ~t, J=12 Hz, 4β-H), 2.64 (1H, dd, J=12.7, 4.5 Hz, 4α-H), 2.80 (2H, br d, J=12.7 Hz, 9β-H), 2.90 (1H, br d, J=13.5 Hz, 10α-H), 3.95–4.1 (3H, br m, 2α—$CH_2OH$ and 3α-H), 4.23 (1H, m, w/2=11 Hz, 1β-H), 5.79 and 6.41 (1H and 1H, each d, J=1.1 Hz, 7- and 6-H); MS m/z (relative intensity) 434 ($M^+$, 37), 416 (33), 398 (16), 383 (10), 305 (12), 287 (25), 269 (26), 245 (40), 69 (100), 59 (74); exact mass calcd for $C_{27}H_{46}O_4$ 434.3396, found 434.3397.

21: UV (in EtOH) $\lambda_{max}$ 242, 250.5, 260.5 nm; $^1$H NMR ($CDCl_3$) δ 0.553 (3H, s, 18-$H_3$), 0.942 (3H, d, J=6.5 Hz, 21-$H_3$), 1.220 (6H, s, 26- and 27-$H_3$), 2.31 (1H, br d, J=14 Hz, 4β-H), 2.45 (1H, br d, J=14 Hz, 4α-H), 2.79 (1H, br d, J=13 Hz, 9β-H), 3.17 (1H, dd, J=12.8, 4.2 Hz, 10β-H), 3.95–4.1 (3H, br m, 1β-H and 2β—$CH_2OH$), 4.17 (1H, m, w/2=10 Hz, 3α-H), 5.89 and 6.26 (1H and 1H, each d, J=11.0 Hz, 7- and 6-H); MS m/z (relative intensity) 434 ($M^+$, 50), 416 (46), 398 (20), 383 (11), 305 (14), 287 (26), 269 (30), 245 (50), 69 (100), 59 (75); exact mass calcd for $C_{27}H_{46}O_4$ 434.3396, found 434.3402.

(20S)-1α,25-Dihydroxy-2α- and (20S)-1α,25-Dihydroxy-2,-(hydroxymethyl)-19-norvitamin $D_3$ (22 and 23). The hydroboration of (20S)-vitamin 17 and subsequent oxidation of the organoborane adduct were performed using the procedure analogous to that described above for (20R)-epimer 11. The reaction products were separated by HPLC (6.2 mm×25 cm Zorbax-Sil column, 4 mL/min) using hexane/2-propanol (87.5:12.5) solvent system, and the isomeric 2-hydroxymethyl vitamins 22 and 23 were collected at $R_v$ 40 mL and 47 mL, respectively. Further purification of both products by reversed-phase HPLC (10 mm×25 cm Zorbax-ODS column, 4 mL/min) using methanol/water (9:1) solvent system afforded analytically pure vitamin 22 (9%) and its 2p-isomer 23 (26%) collected at $R_v$ 25 mL and 22 mL, respectively.

22: UV (in EtOH) $\lambda_{max}$ 242.5, 250.5, 261 nm; $^1$H NMR (CDCl$_3$) δ 0.532 (3H, s, 18-H$_3$), 0.853 (3H, d, J=6.6 Hz, 21-H$_3$), 1.214 (6H, s, 26- and 27-H$_3$), 2.13 (1H, br d, J=13.3 Hz, 10β-H), 2.21 (1H, ~t, J=12 Hz, 4β-H), 2.64 (1H, dd, J=12.8, 4.3 Hz, 4α-H), 2.80 (1H, br d, J=12 Hz, 9β-H), 2.90 (1H, br d, J=13.3 Hz, 10α-H), 3.95–4.1 (3H, br m, 2α—CH$_2$OH and 3α-H), 4.24 (1H, m, w/2=10 Hz, 1β-H), 5.81 and 6.43 (1H and 1H, each d, J=11.1 Hz, 7- and 6-H); MS m/z (relative intensity) 434 (M$^+$, 41), 416 (34), 398 (16), 383 (10), 305 (10), 287 (28), 269 (26), 245 (51), 69 (100), 59 (82); exact mass calcd for $C_{27}H_{46}O_4$ 434.3396, found 434.3390.

23: UV (in EtOH) $\lambda_{max}$ 242, 250.5, 260.5 nm; $^1$H NMR (CDCl$_3$) δ 0.551 (3H, s, 18-H$_3$), 0.861 (3H, d, J=6.4 Hz, 21-H$_3$), 1.215 (6H, s, 26- and 27-H$_3$), 2.31 (1H, br d, J=13.7 Hz, 4β-H), 2.45 (1H, br d, J=13.7 Hz, 4α-H), 2.80 (1H, br d, J=12.5 Hz, 9β-H), 3.17 (1H, dd, J=12.7, 4.2 Hz, 10β-H), 3.95–4.1 (3H, br m, 1β-H and 2β—CH$_2$OH), 4.17 (1H, m, w/2=10 Hz, 3α-H), 5.89 and 6.26 (1H and 1H, each d, J=11.1 Hz, 7- and 6-H); MS m/z (relative intensity) 434 (M$^+$, 35), 416 (29), 398 (15), 383 (8), 305 (10), 287 (18), 269 (23), 245 (48), 69 (100), 59 (93); exact mass calcd for $C_{27}H_{46}O_4$ 434.3396, found 434.3408.

BIOLOGICAL ACTIVITY OF 2-METHYL-SUBSTITUTED 19-NOR-1,25-(OH)$_2$D$_3$ COMPOUNDS AND THEIR 20S-ISOMERS

Figure 3:
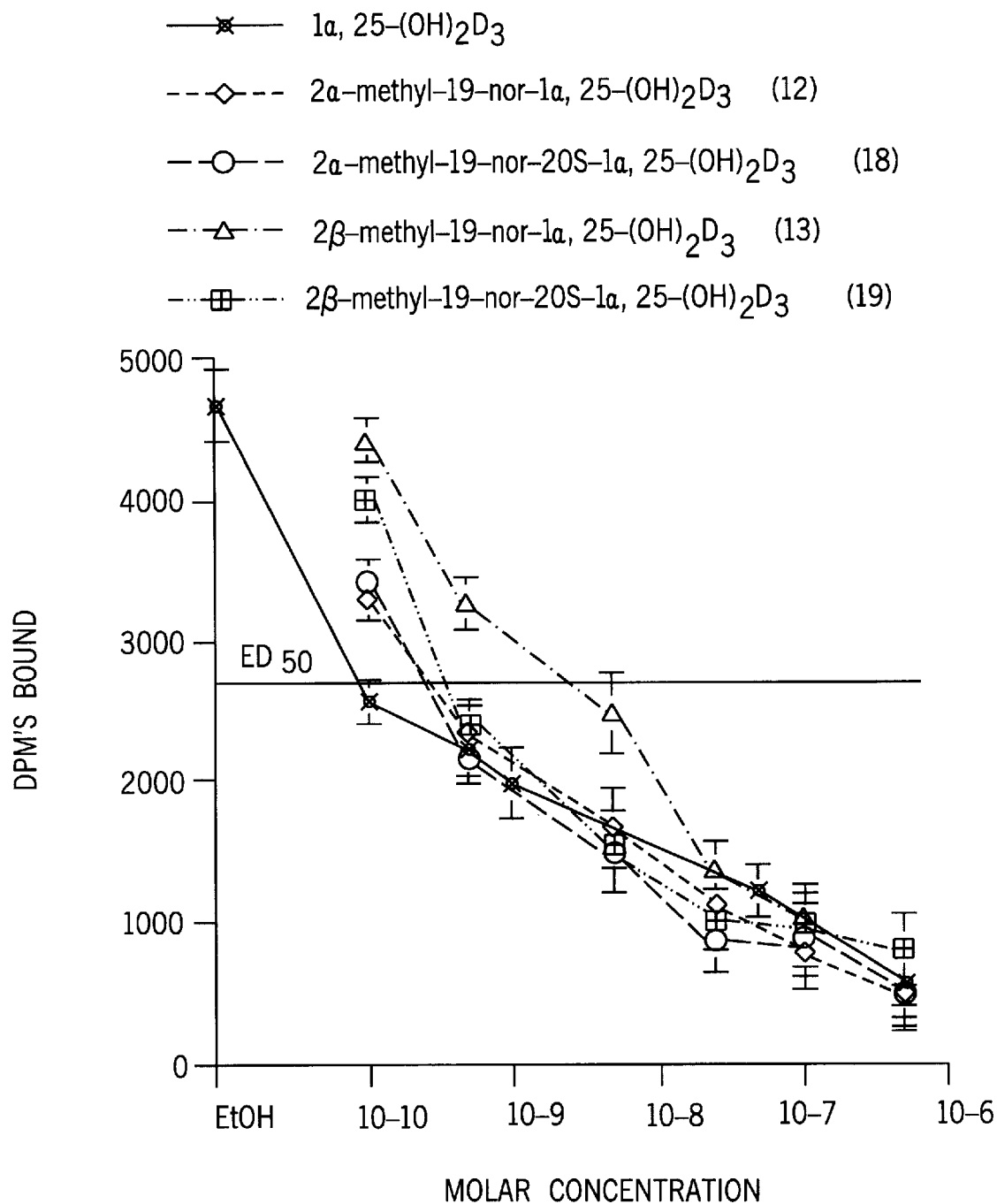
FIG. 3 if a graph similar to FIG. 1 except illustrating the relative activity of the individual compounds 2α and 2β-methyl-19-nor-20S-1α,25-dihydroxyvitamin $D_3$, 2α and 2β-methyl-19-nor-1α,25-dihydroxyvitamin $D_3$ and 1α,25-dihydroxyvitamin $D_3$ to compete for binding of $[^3H]$-1,25-$(OH)_2$-$D_3$ to the vitamin D pig intestinal nuclear receptor.
Figure 5:
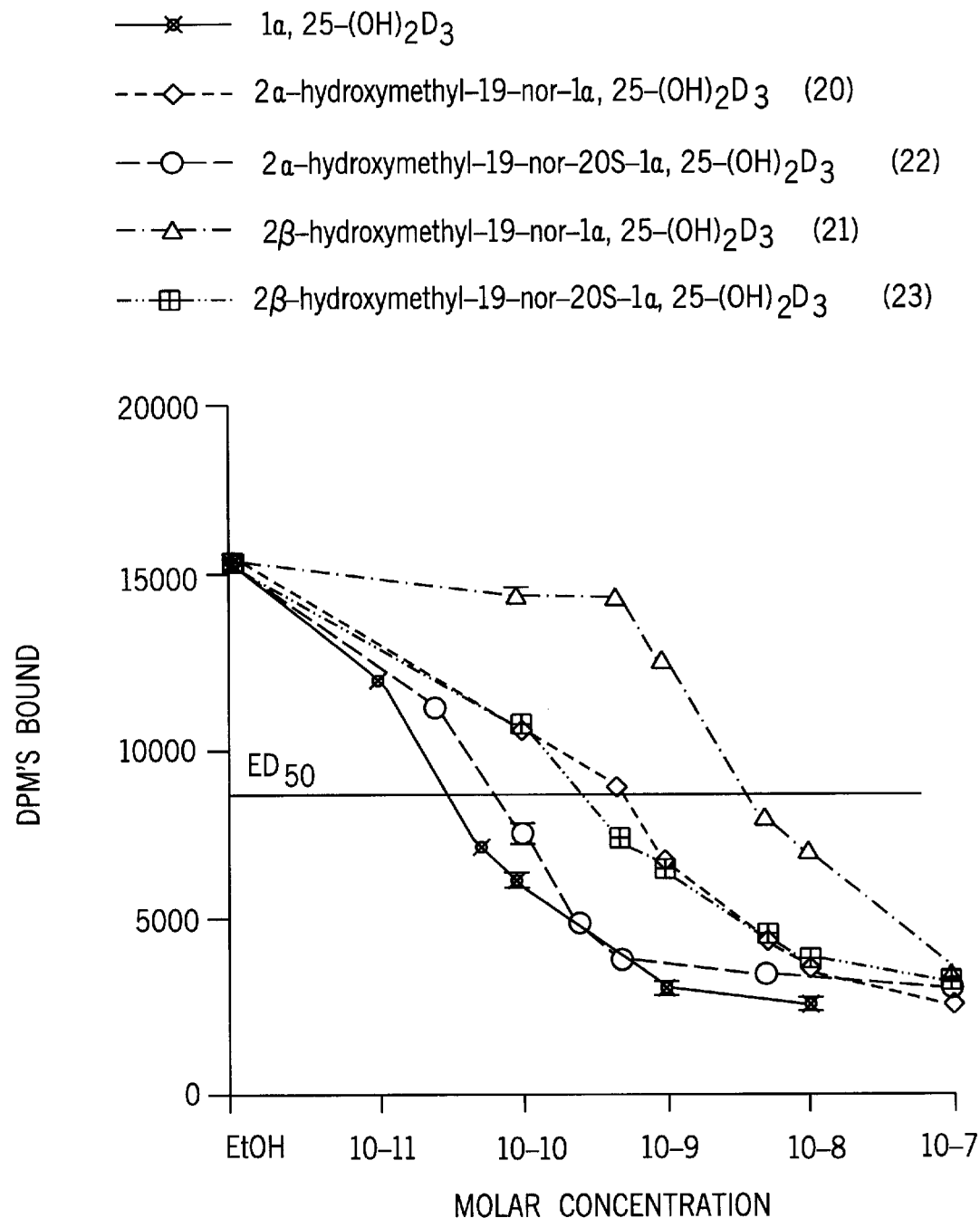
FIG. 5 is a graph illustrating the relative activity of the individual compounds 2α and 2β-hydroxymethyl-19-nor-20S-1α,25-dihydroxyvitamin $D_3$, 2α and 2β-hydroxymethyl-19-nor-1α,25-dihydroxyvitamin $D_3$ and 1α,25-dihydroxyvitamin $D_3$ to complete for binding of $[^3H]$-1,25-$(OH)_2$-$D_3$ to the vitamin D pig intestinal nuclear receptor.
Figure 6:
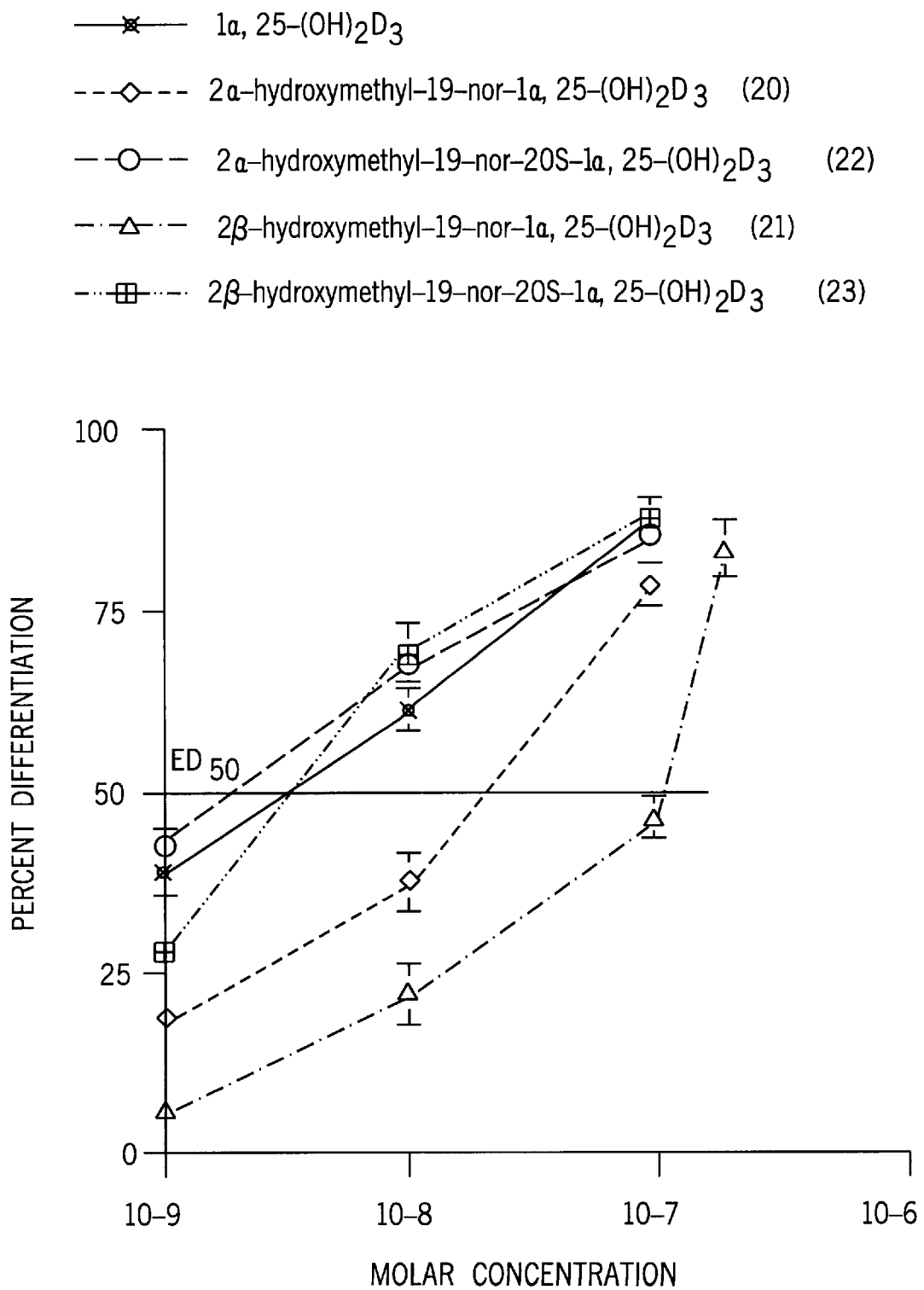
FIG. 6 is a graph illustrating the percent HL-60 cell differentiation as a function of the concentration of the individual compounds 2α and 2β-hydroxymethyl-19-nor-20S-1α,25-dihydroxyvitamin $D_3$, 2α and 2β-hydroxymethyl-19-nor-1α,25-dihydroxyvitamin $D_3$ and 1α,25-dihydroxyvitamin $D_3$.

The synthesized 2-substituted vitamins were tested for their ability to bind the porcine intestinal vitamin D receptor (See FIGS. 1, 3 and 5). A comparison between the natural hormone 1α,25-(OH)$_2$D$_3$ and 2-methyl substituted 19-norvitamins 12, 18 and 19 shows that they are about as active as 1α,25-(OH)$_2$D$_3$, while the 2,β-methyl isomer in the 20R-series 13 is 39-fold less effective. The 2α-hydroxymethyl vitamin D analog 22 with the "unnatural" configuration at C-20 was almost equivalent to 1α,25-(OH)$_2$D$_3$ with respect to receptor binding, and the isomeric 23 proved to be less potent (6–8×) than these compounds. The corresponding 2α-hydroxymethyl analog, possessing the "natural" 20R-configuration 20 exhibited about the same binding affinity as 23, whereas the 2β-isomer 21 was ca. 8 times less effective. The foregoing results of the competitive binding analysis show that vitamins with the axial orientation of the 1α-hydroxy group exhibit a significantly enhanced affinity for the receptor.

It might be expected from these results that all of these compounds would have equivalent biological activity. Surprisingly, however, the 2-methyl substitutions produced highly selective analogs with their primary action on bone. When given for 7 days in a chronic mode, the most potent compounds tested were a mixture of the α and β isomers of 2-methyl 19-nor-20S-1,25-(OH)$_2$D$_3$ (Table 1). When given at 130 pmol/day, the activity of this mixture of compounds on bone calcium mobilization (serum calcium) was much higher than that of the native hormone, possibly as high as 10 or 100 times higher. Under identical conditions, twice the dose of 1,25-(OH)$_2$D$_3$ gave a serum calcium value of 7.2 mg/100 ml, while a mixture of 2-methyl-(α and β)-19-nor-20S-1,25-(OH)$_2$D$_3$ gave a value of 9.6 mg/100 ml of serum calcium at the 130 pmol dose. When given at 260 pmol/day, this mixture produced the astounding value of 12.2 mg/100 ml of serum calcium at the expense of bone. To show its selectivity, these compounds produced no significant change in intestinal calcium transport at 130 pmol dose level while having a strong bone calcium mobilizing activity. At the higher dose, the 2-methyl-20S mixture did produce an intestinal transport response but gave an enormous bone mobilization response. A mixture of the α and β isomers of 2-methyl-19-nor-1,25-(OH)$_2$D$_3$ also had strong bone calcium mobilization at both dose levels but also showed no intestinal calcium transport activity. Thus, the 2-methyl-α and β derivatives given as a mixture showed strong preferential bone calcium mobilizing activity especially when the side chain was in the 20S-configuration. These results illustrate that the 2-methyl and the 20S-2-methyl derivatives of 19-nor-1,25-(OH)$_2$D$_3$ are selective for the mobilization of calcium from bone. Table 2 illustrates the response of both intestine and serum calcium to a single large dose of the various compounds; again, supporting the conclusions derived from Table 1.

Figure 2:
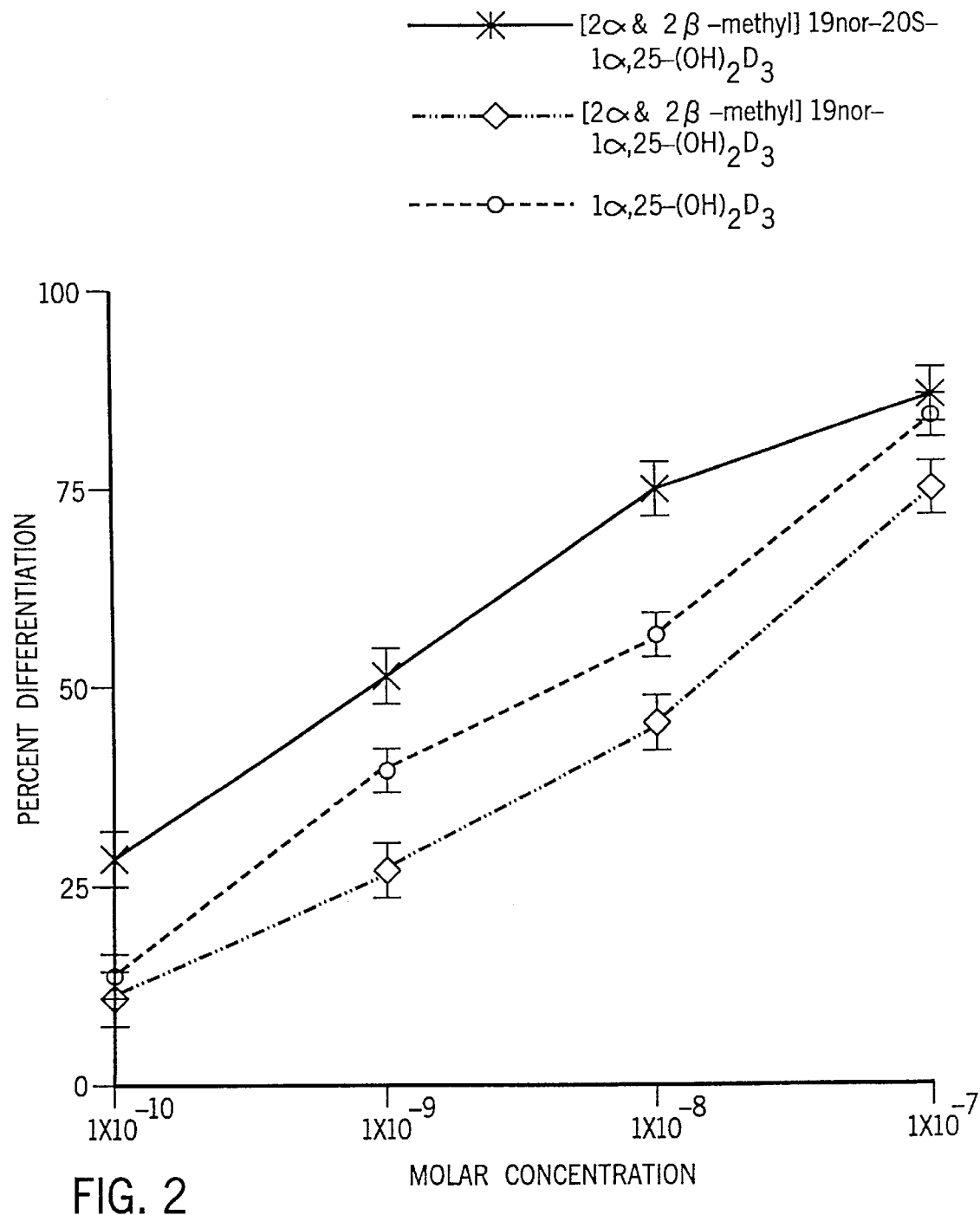
FIG. 2 is a graph illustrating the percent HL-60 cell differentiation as a function of the concentration of a mixture of 2α and 2β-methyl-19-nor-20S-1α,25-dihydroxyvitamin $D_3$, a mixture of 2α and 2β-methyl-19-nor-1,α25-dihydroxyvitamin $D_3$ and 1α,25-dihydroxyvitamin $D_3$.

The results in FIG. 2 illustrate that a mixture of the α and β derivatives of 2-methyl-19-nor-20S-1,25-(OH)$_2$D$_3$ is extremely potent in inducing differentiation of HL-60 cells to the moncyte. The 2-methyl-α and β compounds had activity similar to 1,25-(OH)$_2$D$_3$. These results illustrate the potential of the 2-methyl-19-nor-20S-1,25-(OH)$_2$D$_3$ compounds as anti-cancer agents, especially against leukemia, colon cancer, breast cancer and prostate cancer, or as agents in the treatment of psoriasis.

Competitive binding of the analogs to the porcine intestinal receptor was carried out by the method described by Dame et al (Biochemistry 25, 4523–4534, 1986).

The differentiation of HL-60 promyelocytic into monocytes was determined as described by Ostrem et al (J. Biol. Chem. 262, 14164–14171, 1987).

TABLE 1

Response of Intestinal Calcium Transport and Serum Calcium (Bone Calcium Mobilization) Activity to Chronic Doses of 2-Methyl Derivatives of 19-Nor-1,25-(OH)$_2$D$_3$ and its 20S Isomers

| Group | Dose (pmol/day/7 days) | Intestinal Calcium Transport (S/M) | Serum Calcium (mg/100 ml) |
|---|---|---|---|
| Vitamin D Deficient | Vehicle | 5.5 ± 0.2 | 5.1 ± 0.16 |
| 1,25-(OH)$_2$D$_3$ Treated | 260 | 6.2 ± 0.4 | 7.2 ± 0.5 |
| 2-Methyl (α and β) | 130 | 5.0 ± 0.3 | 6.1 ± 0.1 |
| 19-Nor-1,25-(OH)$_2$D$_3$ | 260 | 5.3 ± 0.6 | 6.7 ± 0.4 |
| 2-Methyl (α and β) | 130 | 5.0 ± 0.9 | 9.6 ± 0.1 |
| 19-Nor-20S-1,25-(OH)$_2$D$_3$ | 260 | 6.9 ± 0.5 | 12.2 ± 0.3 |

Male weanling rats were obtained from Sprague Dawley Co. (Indianapolis, Ind.) and fed a 0.47% calcium, 0.3% phosphorus vitamin D-deficient diet for 1 week and then given the same diet containing 0.02% calcium, 0.3% phosphorus for 2 weeks. During the last week they were given the indicated dose of compound by intraperitoneal injection in 0.1 ml 95% propylene glycol and 5% ethanol each day for 7 days. The control animals received only the 0.1 ml of 95% propylene glycol, 5% ethanol. Twenty-four hours after the last dose, the rats were sacrificed and intestinal calcium transport was determined by everted sac technique as previously described and serum calcium determined by atomic absorption spectrometry on a model 3110 Perkin Elmer instrument (Norwalk, Conn.). There were 5 rats per group and the values represent mean±SEM.

TABLE 2

Response of Intestinal Calcium Transport and Serum Calcium (Bone Calcium Mobilization) Activity to a Single Dose of 2-Methyl-Derivatives of 19-Nor-1,25-(OH)$_2$D$_3$ and its 20S Isomers

| Group | Intestinal Calcium Transport (S/M) | Serum Calcium (mg/100 ml) |
|---|---|---|
| -D Control | 4.2 ± 0.3 | 4.7 ± 0.1 |
| 1,25-(OH)$_2$D$_3$ | 5.8 ± 0.3 | 5.7 ± 0.2 |
| 2-Methyl (α and β mixture)-19-Nor-1,25-(OH)$_2$D$_3$ | 3.6 ± 0.4 | 5.4 ± 0.1 |
| 2-Methyl (α and β mixture)-19-Nor-20S-1,25-(OH)$_2$D$_3$ | 6.7 ± 0.6 | 8.1 ± 0.3 |

Male Holtzman strain weanling rats were obtained from the Sprague Dawley Co. (Indianapolis, Ind.) and fed the 0.47% calcium, 0.3% phosphorus diet described by Suda et al. (J. Nutr. 100, 1049–1052, 1970) for 1 week and then fed the same diet containing 0.02% calcium and 0.3% phosphorus for 2 additional weeks. At this point, they received a single intrajugular injection of the indicated dose dissolved in 0.1 ml of 95% propylene glycol/5% ethanol. Twenty-four hours later they were sacrificed and intestinal calcium transport and serum calcium were determined as described in Table 1. The dose of the compounds was 650 pmol and there were 5 animals per group. The data are expressed as mean±SEM.

When given for 7 days in a chronic mode, the most potent individual compound tested was 2α-methyl 19-nor-20S-1,25-(OH)$_2$D$_3$ (Table 3). When given at 130 pmol/day, the activity of this compound on bone calcium mobilization (serum calcium) was much higher than that of the native hormone, possibly as high as 10 or 100 times higher. Under identical conditions, twice the dose of 1,25-(OH)$_2$D$_3$ gave a serum calcium value of 6.6 f 0.4 mg/100 ml, while 2α-methyl-19-nor-20S-1,25-(OH)$_2$D$_3$ gave a value of 8.3±0.7 mg/100 ml of serum calcium at the 130 pmol dose. When given at 260 pmol/day, 2α-methyl-19-nor-20S-1,25-(OH)$_2$D$_3$ produced the astounding value of 10.3±0.11 mg/100 ml of serum calcium at the expense of bone. To show its selectivity, this compound also produced a significant change in intestinal calcium transport at both the 260 pmol and the 130 pmol dose levels while having a strong bone calcium mobilizing activity. At the higher dose, the 2α-methyl-20S compound did produce a significant intestinal transport response but also gave an enormous bone mobilization response. With respect to the 2,-methyl-i 9-nor-20S compound, the data in Table 3 show it has little, if any, intestinal calcium transport activity, and little, if any, bone mobilization activity. The data in Table 4 illustrate that 2α-methyl-19-nor-1,25-(OH)$_2$D$_3$ also had relatively strong bone calcium mobilization at both dose levels and also showed some intestinal calcium transport activity. In contrast, 2β-methyl-19-nor-1,25-(OH)$_2$D$_3$ showed little, if any, intestinal calcium transport or bone calcium mobilization activities. Thus, the 2α-methyl-19-nor derivative showed strong preferential bone calcium mobilizing activity especially when the side chain was in the 20S-configuration. These results illustrate that the 2α-methyl and the 20S-2α-methyl derivatives of 19-nor-1,25-(OH)$_2$D$_3$ are selective for the mobilization of calcium from bone.

Figure 4:
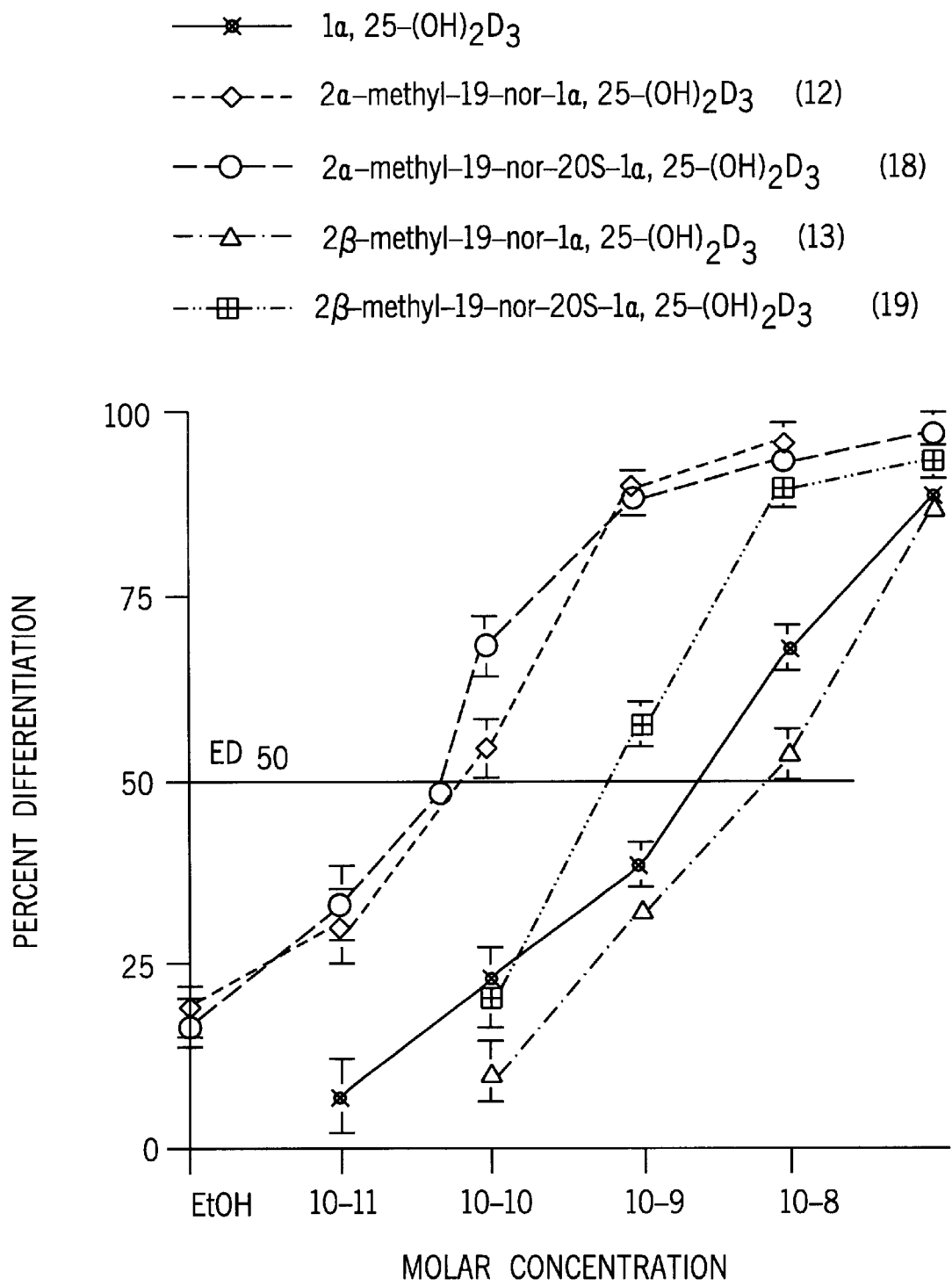
FIG. 4 is a graph similar to FIG. 2 except illustrating the percent HL-60 cell differentiation as a function of the concentration of the individual compounds 2α and 2β-methyl-19-nor-20S-1α,25-dihydroxyvitamin $D_3$, 2α and 2β-methyl-19-nor-1α,25-dihydroxyvitamin $D_3$ and 1α,25-dihydroxyvitamin $D_3$.

The results in FIG. 4 illustrate that 2α-methyl-19-nor-20S-1,25-(OH)$_2$D$_3$ and 2α-methyl-19-nor-1,25-(OH)$_2$D$_3$ are extremely potent in inducing differentiation of HL-60 cells to the monocyte. The 2β-methyl compounds had activity similar to 1,25-(OH)$_2$D$_3$. These results illustrate the potential of the 2α-methyl-19-nor-20S-1,25-(OH)$_2$D$_3$ compound as an anti-cancer agent, especially against leukemia, colon cancer, breast cancer and prostate cancer, or as an agent in the treatment of psoriasis.

Competitive binding of the analogs to the porcine intestinal receptor was carried out by the method described by Dame et al (Biochemistry 25, 4523–4534, 1986).

The differentiation of HL-60 promyelocytic into monocytes was determined as described by Ostrem et al (J. Biol. Chem. 262, 14164–14171, 1987).

TABLE 3

Response of Intestinal Calcium Transport and Serum Calcium (Bone Calcium Mobilization) Activity to Chronic Doses of the 20S Isomers of 2-Methyl Derivatives of 19-Nor-1,25-(OH)$_2$D$_3$

| Group | Dose (pmol/day/7 days) | Intestinal Calcium Transport (S/M) | Serum Calcium (mg/100 ml) |
|---|---|---|---|
| Vitamin D Deficient | Vehicle | 2.9 ± 0.2 | 4.2 ± 0.1 |
| 1,25-(OH)$_2$D$_3$ Treated | 260 | 4.6 ± 0.2 | 6.6 ± 0.4 |
| 2α-Methyl-19-nor-(20S)-1,25-(OH)$_2$D$_3$ | 130 | 12.9 ± 1.9 | 8.3 ± 0.7 |
|  | 260 | 8.4 ± 1.1 | 10.3 ± 0.11 |
| 2β-Methyl-19-nor-(20S)-1,25-(OH)$_2$D$_3$ | 130 | 2.9 ± 0.3 | 4.4 ± 0.1 |
|  | 260 | 3.8 ± 0.1 | 4.4 ± 0.1 |

With respect to the data in Tables 3 and 4, male weanling rats were obtained from Sprague Dawley Co. (Indianapolis, Ind.) and fed a 0.47% calcium, 0.3% phosphorus vitamin D-deficient diet for 1 week and then given the same diet containing 0.02% calcium, 0.3% phosphorus for 2 weeks. During the last week they were given the indicated dose of compound by intraperitoneal injection in 0.1 ml 95% propylene glycol and 5% ethanol each day for 7 days. The control animals received only the 0.1 ml of 95% propylene glycol, 5% ethanol. Twenty-four hours after the last dose, the rats were sacrificed and intestinal calcium transport was determined by everted sac technique as previously described and serum calcium determined by atomic absorption spectrometry on a model 3110 Perkin Elmer instrument (Norwalk, Conn.). There were 5 rats per group and the values represent mean±SEM.

TABLE 4

Response of Intestinal Calcium Transport and Serum Calcium (Bone Calcium Mobilization) Activity to Chronic Doses of the 2-Methyl-Derivatives of 19-Nor-1,25-(OH)$_2$D$_3$

| Group | Dose Pmol/day/7 days | Intestinal Calcium Transport (S/M) | Serum Calcium (mg/100 ml) |
|---|---|---|---|
| -D Control | 0 | 2.3 ± 0.8 | 3.9 ± 0.2 |
| 1,25-(OH)$_2$D$_3$ | 260 | 5.6 ± 1.3 | 6.1 ± 0.5 |
| 2α-Methyl-19-nor-1,25-(OH)$_2$D$_3$ | 130 | 4.3 ± 1.0 | 4.8 ± 0.2 |
|  | 260 | 5.3 ± 1.3 | 5.8 ± 0.5 |
| 2β-Methyl-19-nor-1,25-(OH)$_2$D$_3$ | 130 | 4.4 ± 0.8 | 4.1 ± 0.1 |
|  | 260 | 3.1 ± 0.9 | 3.8 ± 0.2 |

Table 5 provides intestinal calcium transport and bone calcium mobilization data for 2-hydroxymethyl derivatives of 19-nor-1α,25-(OH)$_2$D$_3$. These derivatives turned out to be relatively inactive, including those in the 20S-series 22 and 23.

TABLE 5

Response of Intestinal Calcium Transport and Serum Calcium (Bone Calcium Mobilization) Activity to Chronic Doses of the 2-Hydroxymethyl-Derivatives of 19-Nor-1,25-(OH)$_2$D$_3$

| Group | Dose Pmol/day/7 days | Intestinal Calcium Transport (S/M) | Serum Calcium (mg/100 ml) |
|---|---|---|---|
| Vitamin D Deficient | Vehicle | 4.0 ± 0.3 | 3.8 ± 0.1 |
| 1,25-(OH)$_2$D$_3$ Treated | 260 | 6.6 ± 0.5 | 5.2 ± 0.1 |
| 2α-Hydroxy-methyl-19-nor-(20S)-1,25-(OH)$_2$D$_3$ | 130 | 5.0 ± 0.3 | 4.0 ± 0.1 |
|  | 260 | 5.8 ± 0.4 | 3.9 ± 0.1 |
| 2β-Hydroxy-methyl-19-nor-(20S)-1,25-(OH)$_2$D$_3$ | 130 | 3.5 ± 0.7 | 3.6 ± 0.1 |
|  | 260 | 3.5 ± 0.3 | 3.5 ± 0.2 |

In the next assay, the cellular activity of the synthesized compounds was established by studying their ability to induce differentiation of human promyelocyte HL-60 cells into monocytes. It was found that all of the synthesized vitamin D analogs with the "unnatural" 20S-configuration were more potent than 1α,25-(OH)$_2$D$_3$. Moreover, the same relationship between cellular activity and conformation of the vitamin D compounds was established as in the case of receptor binding analysis and in vivo studies, i.e. 2α-substituted vitamin D analogs were considerably more active than their 2β-substituted counterparts with the equatorially oriented 1α-hydroxy group. Thus, 2α-methyl vitamins 12 and 18 proved to be 100 and 10 times, respectively, more active than their corresponding 2D-isomers 13 and 19 in the cultures of HL-60 in vitro, whereas in the case of 2-hydroxymethyl derivatives (20, 22 versus 21, 23) these differences were slightly smaller. Since vitamins with 2β-methyl substituent (13, 19) and both 2-hydroxymethyl analogs in 20S-series (22, 23) have selective activity profiles combining high potency in cellular differentiation, and lack of calcemic activity, such compounds are potentially useful as therapeutic agents for the treatment of cancer.

These results indicate that variation of substituents on C-2 in the parent 19-nor-1α,25-dihydroxyvitamin D$_3$ can change completely (and selectively) the biological potency of the analogs. These results suggest that 2α-methyl-19-nor-20S-1,25-(OH)$_2$D$_3$ has preferential activity on bone, making it a candidate for treatment of bone disease.

For treatment purposes, the novel compounds of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds may be administered orally, topically, parenterally, sublingually, intranasally, or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. Doses of from 0.1 μg to 50 μg per day of the compounds are appropriate for treatment purposes, such doses being adjusted according to the disease to be treated, its severity and the response of the subject as is well understood in the art. Since the new compounds exhibit specificity of action, each may be suitably administered alone, or together with graded doses of another active vitamin D compound—e.g. 1α-hydroxyvitamin D$_2$ or D$_3$, or 1α,25-dihydroxyvitamin D$_3$—in situations where different degrees of bone mineral mobilization and calcium transport stimulation is found to be advantageous.

Compositions for use in the above-mentioned treatment of psoriasis and other malignancies comprise an effective amount of one or more 2-substituted-19-nor-vitamin D compound as defined by the above formula I as the active ingredient, and a suitable carrier. An effective amount of such compounds for use in accordance with this invention is from about 0.01 μg to about 100 μg per gm of composition, and may be administered topically, transdermally, orally, sublingually, intranasally, or parenterally in dosages of from about 0.1 μg/day to about 100 μg/day.

The compounds may be formulated as creams, lotions, ointments, topical patches, pills, capsules or tablets, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds are advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For asthma treatment, inhalation of powder, self-propelling or spray formulations, dispensed with a spray can, a nebulizer or an atomizer can be used. The formulations, when dispensed, preferably have a particle size in the range of 10 to 100 μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

In its broadest application, the present invention relates to any 19-nor-2-alkyl analogs of vitamin D which have the vitamin D nucleus. By vitamin D nucleus, it is meant a central part consisting of a substituted chain of five carbon atoms which correspond to positions 8, 14, 13, 17 and 20 of vitamin D, and at the ends of which are connected at position 20 a structural moiety representing any of the typical side chains known for vitamin D type compounds (such as R as previously defined herein), and at position 8 the 5,7-diene moiety connected to the A-ring of an active 1α-hydroxy vitamin D analog (as illustrated by formula I herein). Thus, various known modifications to the six-membered C-ring and the five-membered D-ring typically present in vitamin D, such as the lack of one or the other or both, are also embraced by the present invention.

Accordingly, compounds of the following formulae Ia, are along with those of formula I, also encompassed by the present invention:

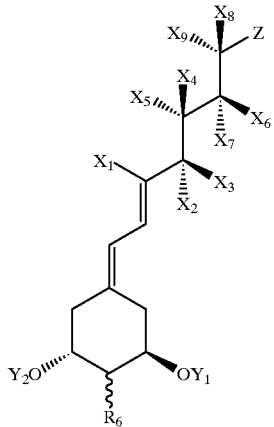

Ia

In the above formula Ia, the definitions of $Y_1$, $Y_2$, $R_6$, and Z are as previously set forth herein. With respect to $X_1$, $X_2$, $X_3$, $X_4$, $X_5$, $X_6$, $X_7$, $X_8$ and $X_9$, these substituents may be the same or different and are selected from hydrogen or lower alkyl, i.e. a $C_{1-5}$ alkyl such as methyl, ethyl or n-propyl. In addition, paired substituents $X_1$ and $X_4$ or $X_5$, $X_2$ or $X_3$ and $X_6$ or $X_7$, $X_4$ or $X_5$ and $X_8$ or $X_9$, when taken together with the three adjacent carbon atoms of the central part of the compound, which correspond to positions 8, 14, 13 or 14, 13, 17 or 13, 17, 20 respectively, can be the same or different and form a saturated or unsaturated, substituted or unsubstituted, carbocyclic 3, 4, 5, 6 or 7 membered ring.

Preferred compounds of the present invention may be represented by one of the following formulae:

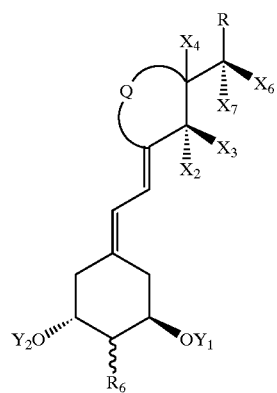

Ib

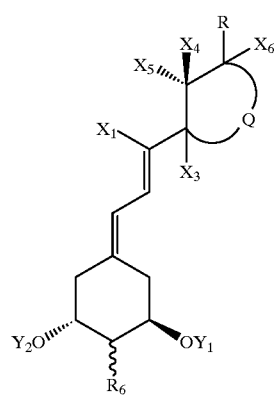

Ic

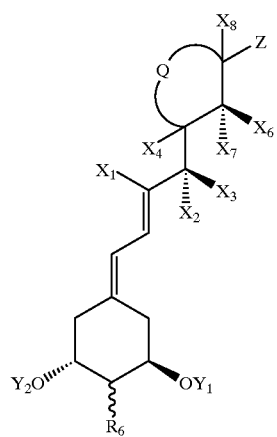

Id

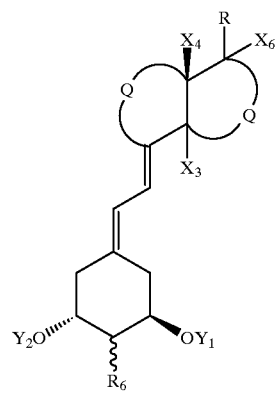

Ie

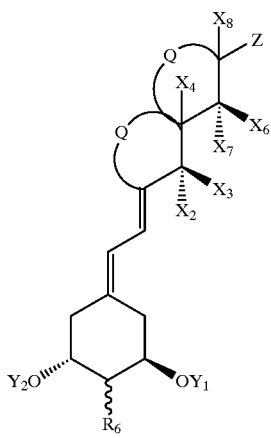

If

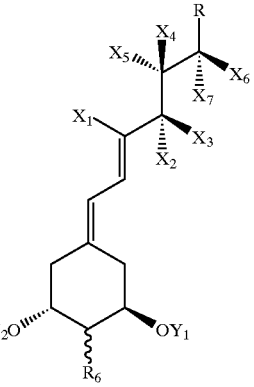

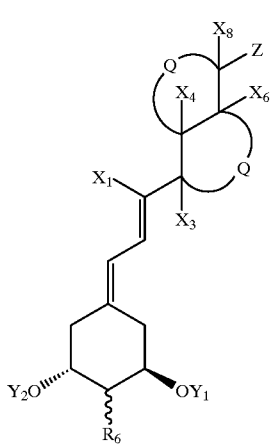

Ig

In the above formulae Ib, Ic, Id, Ie, If, Ig and Ih, the definitions of $Y_1$, $Y_2$, $R_6$, R, Z, $X_1$, $X_2$, $X_3$, $X_4$, $X_5$, $X_6$, $X_7$ and $X_8$ are as previously set forth herein. The substituent Q represents a saturated or unsaturated, substituted or unsubstituted, hydrocarbon chain comprised of 0, 1, 2, 3 or 4 carbon atoms, but is preferably the group —$(CH_2)_k$— where k is an integer equal to 2 or 3.

Methods for making compounds of formulae Ia-Ih are known. Specifically, reference is made to International Application Number PCT/EP94/02294 filed Jul. 7, 1994 and published Jan. 19, 1995 under International Publication Number WO95/01960.

SCHEME I

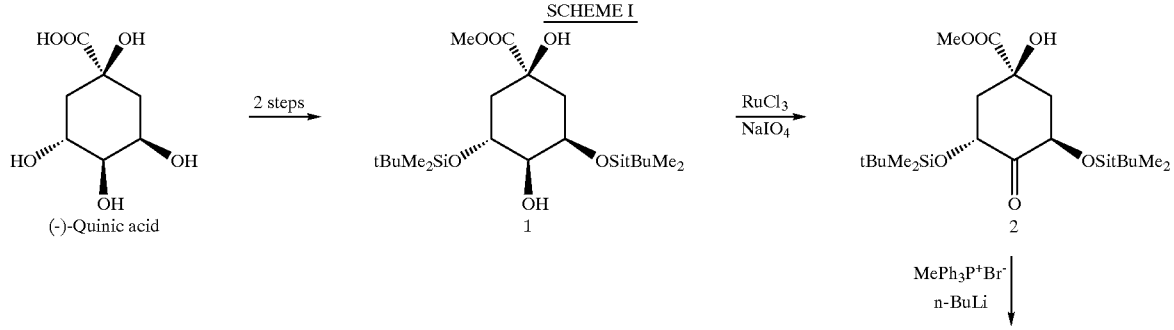

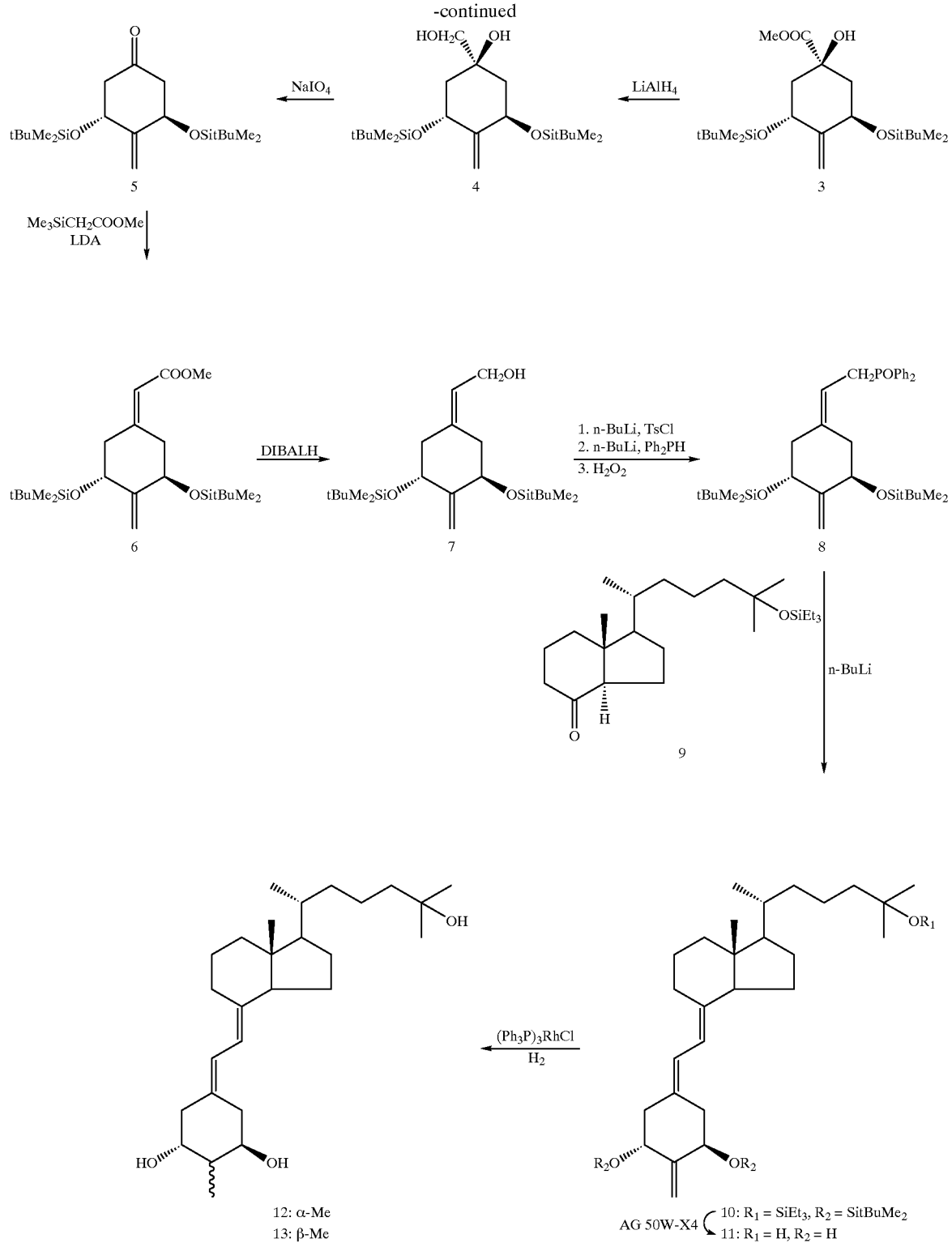

31 SCHEME II 32
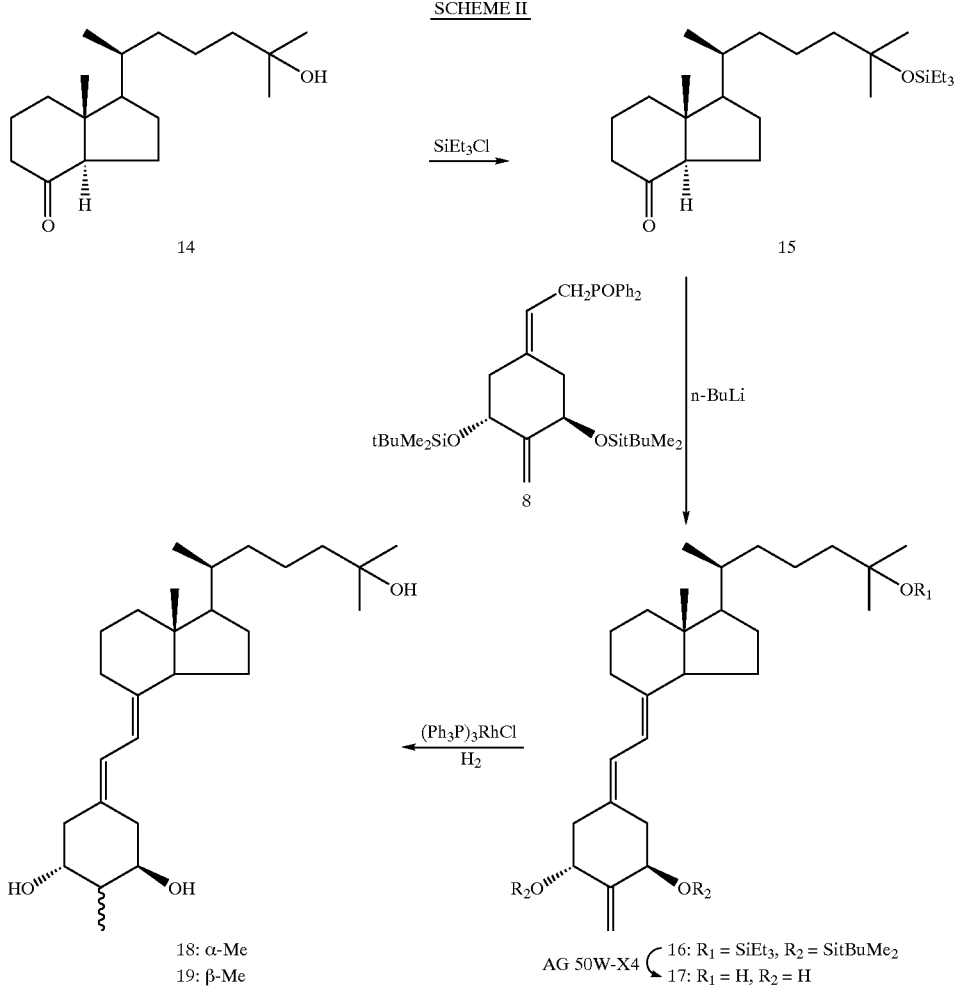
SCHEME III
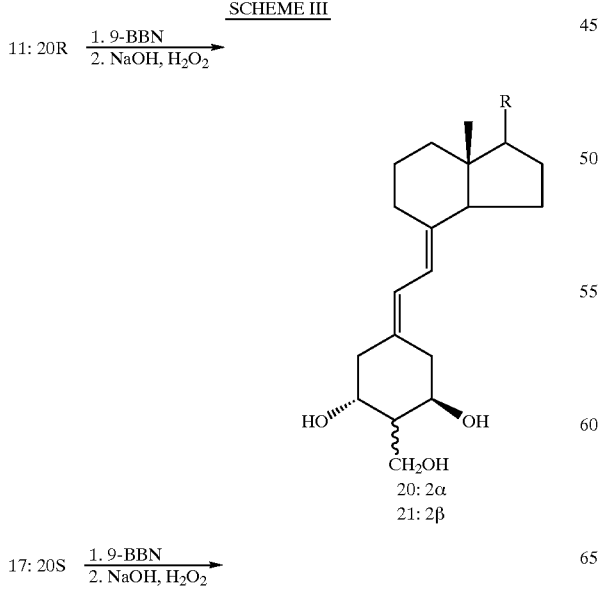
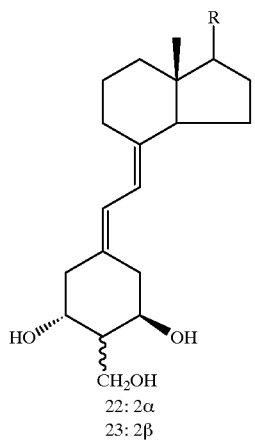
-continued

I claim:
1. A compound having the formula:

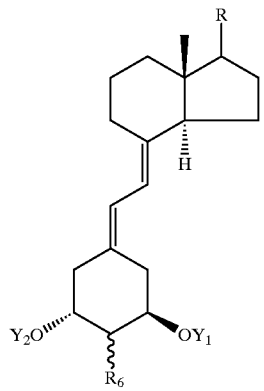

where $Y_1$ and $Y_2$, which may be the same or different, are each selected from the group consisting of hydrogen and a hydroxy-protecting group, $R_6$ is selected from alkyl, hydroxyalkyl and fluoroalkyl, and where the group R is represented by the structure:

where the stereochemical center at carbon 20 may have the R or S configuration, and where Z is selected from Y, —OY, —CH$_2$OY, —C≡CY and —CH=CHY, where the double bond may have the cis or trans geometry, and where Y is selected from hydrogen, methyl, —COR$^5$ and a radical of the structure:

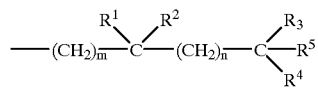

where m and n, independently, represent the integers from 0 to 5, where $R^1$ is selected from hydrogen, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group, =CR$^2$R$^3$, or the group —(CH$_2$)$_p$—, where p is an integer from 2 to 5, and where $R^3$ and $R^4$, taken together, represent an oxo group, or the group —(CH$_2$)$_q$—, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —CH(CH$_3$)—, —CH(R$^3$)—, or —CH(R$^2$)— at positions 20, 22, and 23, respectively, may be replaced by an oxygen or sulfur atom.

2. The compound of claim 1 where R is a side chain of the formula

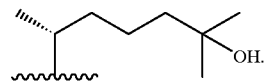

3. The compound of claim 1 where R is a side chain of the formula

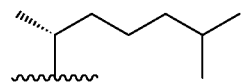

4. The compound of claim 1 where R is a side chain of the formula

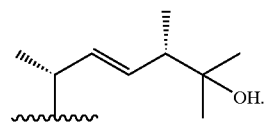

5. The compound of claim 1 where R is a side chain of the formula

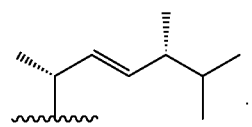

6. The compound of claim 1 where R is a side chain of the formula

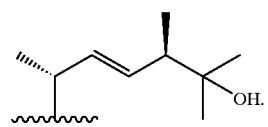

7. The compound of claim 1 where R is a side chain of the formula

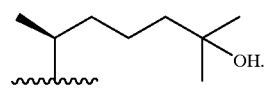

8. The compound of claim 1 where R is a side chain of the formula

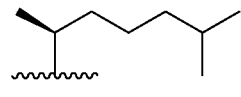

9. The compound of claim 1 where R is a side chain of the formula

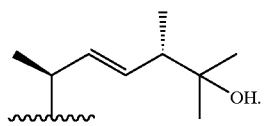

10. The compound of claim 1 where R is a side chain of the formula

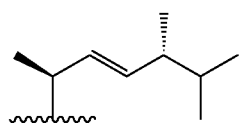

11. The compound of claim 1 where R is a side chain of the formula

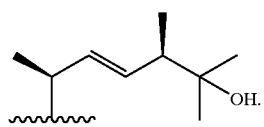

12. 2α-hydroxymethyl-19-nor-1α,25-dihydroxyvitamin $D_3$.
13. 2β-hydroxymethyl-19-nor-1α,25-dihydroxyvitamin $D_3$.
14. 2α-hydroxymethyl-19-nor-20(S)-1α,25-dihydroxyvitamin $D_3$.
15. 2β-hydroxymethyl-19-nor-20(S)-1α,25-dihydroxyvitamin $D_3$.
16. A pharmaceutical composition containing at least one compound as claimed in claim 1 together with a pharmaceutically acceptable excipient.
17. The pharmaceutical composition of claim 16 containing 2α-methyl-19-nor-1α,25-dihydroxyvitamin $D_3$ in an amount from about 0.1 μg to about 50 μg.
18. The pharmaceutical composition of claim 16 containing 2β-methyl-19-nor-1α,25-dihydroxyvitamin $D_3$ in an amount from about 0.1 μg to about 50 μg.
19. The pharmaceutical composition of claim 16 containing 2α-methyl-19-nor-20(S)-1α,25-dihydroxyvitamin $D_3$ in an amount from about 0.1 μg to about 50 μg.
20. The pharmaceutical composition of claim 16 containing 2β-methyl-19-nor-20(S)-1α,25-dihydroxyvitamin $D_3$ in an amount from about 0.1 μg to about 50 μg.
21. The pharmaceutical composition of claim 16 containing 2α-hydroxymethyl-19-nor-1α,25-dihydroxyvitamin $D_3$ in an amount from about 0.1 μg to about 50 μg.
22. The pharmaceutical composition of claim 16 containing 2β-hydroxymethyl-19-nor-1α,25-dihydroxyvitamin $D_3$ in an amount from about 0.1 μg to about 50 μg.
23. The pharmaceutical composition of claim 16 containing 2α-hydroxymethyl-19-nor-20(S)-1α,25-dihydroxyvitamin $D_3$ in an amount from about 0.1 μg to about 50 μg.
24. The pharmaceutical composition of claim 16 containing 2β-hydroxymethyl-19-nor-20(S)-1α,25-dihydroxyvitamin $D_3$ in an amount from about 0.1 μg to about 50 μg.
25. The pharmaceutical composition of claim 16 containing a mixture of 2α-methyl-19-nor-1α,25-dihydroxyvitamin $D_3$ and 2 β-methyl-19-nor-1α,25-dihydroxyvitamin $D_3$.

26. The pharmaceutical composition of claim 16 containing a mixture of 2α-methyl-19-nor-20(S)-1α,25-dihydroxyvitamin $D_3$ and 2β-methyl-19-nor-20(S)-1α,25-dihydroxyvitamin $D_3$.

27. A method of treating metabolic bone disease where it is desired to maintain or increase bone mass comprising administering to a patient with said disease an effective amount of a compound having the formula:

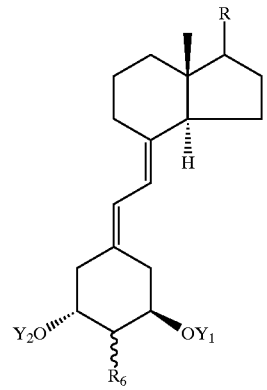

where $Y_1$ and $Y_2$, which may be the same or different, are each selected from the group consisting of hydrogen and a hydroxy-protecting group, $R_6$ is selected from alkyl, hydroxyalkyl and fluoroalkyl, and where the group R is represented by the structure:

where the stereochemical center at carbon 20 may have the R or S configuration, and where Z is selected from Y, —OY, —$CH_2OY$, —C≡CY and —CH=CHY, where the double bond may have the cis or trans geometry, and where Y is selected from hydrogen, methyl, —$COR^5$ and a radical of the structure:

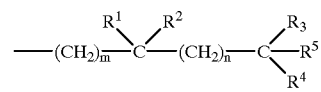

where m and n, independently, represent the integers from 0 to 5, where $R^1$ is selected from hydrogen, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group, =$CR^2R^3$, or the group —$(CH_2)_p$—, where p is an integer from 2 to 5, and where $R^3$ and $R^4$, taken together, represent an oxo group, or the group —$(CH_2)_q$— where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —CH($CH_3$)—, —CH($R^3$)—, or —CH($R^2$)— at positions 20, 22, and 23, respectively, may be replaced by an oxygen or sulfur atom.

28. The method of claim 27 where the disease is senile osteoporosis.

29. The method of claim 27 where the disease is postmenopausal osteoporosis.

30. The method of claim 27 where the disease is steroid-induced osteoporosis.

31. The method of claim 27 where the disease is low bone turnover osteoporosis.

32. The method of claim 27 where the disease is osteomalacia.

33. The method of claim 27 where the disease is renal osteodystrophy.

34. The method of claim 27 wherein the compound is administered orally.

35. The method of claim 27 wherein the compound is administered parenterally.

36. The method of claim 27 wherein the compound is administered transdermally.

37. The method of claim 27 wherein the compound is administered in a dosage of from 0.1 µg to 50 µg per day.

38. The method of claim 27 wherein the compound is 2α-hydroxymethyl-19-nor-1α,25-dihydroxyvitamin $D_3$.

39. The method of claim 27 wherein the compound is 2β-hydroxymethyl-19-nor-1α,25-dihydroxyvitamin $D_3$.

40. The method of claim 27 wherein the compound is 2α-hydroxymethyl-19-nor-20(S)-1α,25-dihydroxyvitamin $D_3$.

41. The method of claim 27 wherein the compound is 2α-hydroxymethyl-19-nor-20(S)-1α,25-dihydroxyvitamin $D_3$.

42. The method of claim 27 wherein a mixture of 2α-methyl-19-nor-1α,25-dihydroxyvitamin $D_3$ and 2β-methyl-19-nor-1α,25-dihydroxyvitamin $D_3$ is administered to said patient.

43. The method of claim 27 wherein a mixture of 2α-methyl-19-nor-20(S)-1α,25-dihydroxyvitamin $D_3$ and 2α-methyl-19-nor-20(S)-1α,25-dihydroxyvitamin $D_3$ is administered to said patient.

* * * * *

UNITED STATES PATENT AND TRADEMARK OFFICE
CERTIFICATE OF CORRECTION

PATENT NO.   : 6,127,559  
DATED        : October 3, 2000  
INVENTOR(S)  : Hector F. DeLuca Page 1 of 1

It is certified that error appears in the above-identified patent and that said Letters Patent is hereby corrected as shown below:

Column 38, claim 41,
Line 9, delete "2α" and substitute therefor -- 2β --

Column 38, claim 43,
Line 17, delete "2α" and substitute therefor -- 2β --

Signed and Sealed this

Fifth Day of February, 2002

Attest:

JAMES E. ROGAN
*Director of the United States Patent and Trademark Office*

*Attesting Officer*